(12) United States Patent
Matsunobu et al.

(10) Patent No.: US 10,674,908 B2
(45) Date of Patent: Jun. 9, 2020

(54) FUNDUS IMAGING APPARATUS

(71) Applicant: NIDEK CO., LTD., Gamagori, Aichi (JP)

(72) Inventors: Go Matsunobu, Aichi (JP); Joji Sasaki, Aichi (JP); Masaaki Hanebuchi, Aichi (JP)

(73) Assignee: NIDEK CO., LTD., Gamagori, Aichi (JP)

( * ) Notice: Subject to any disclaimer, the term of this patent is extended or adjusted under 35 U.S.C. 154(b) by 104 days.

(21) Appl. No.: 15/938,645

(22) Filed: Mar. 28, 2018

(65) Prior Publication Data

US 2018/0289260 A1    Oct. 11, 2018

(30) Foreign Application Priority Data

Mar. 30, 2017  (JP) ................. 2017-069318

(51) Int. Cl.
*A61B 3/12* (2006.01)
*A61B 3/10* (2006.01)
*A61B 3/14* (2006.01)

(52) U.S. Cl.
CPC ............ *A61B 3/1225* (2013.01); *A61B 3/102* (2013.01); *A61B 3/1025* (2013.01); *A61B 3/145* (2013.01)

(58) Field of Classification Search
CPC ........ A61B 3/1225; A61B 3/145; A61B 3/102
See application file for complete search history.

(56) References Cited

FOREIGN PATENT DOCUMENTS

JP          2014-138904 A     7/2014

*Primary Examiner* — Jack Dinh
(74) *Attorney, Agent, or Firm* — Sughrue Mion, PLLC

(57) ABSTRACT

A fundus imaging device includes an objective optical system formed of a plurality of eccentrically disposed mirrors, and an SLO optical system and an OCT optical system which irradiate a fundus with light from a light source via the objective optical system and receive fundus reflected light. The fundus imaging device further includes a correction mirror as a part of the objective optical system, or between the objective optical system and the SLO optical system or the OCT optical system. The correction mirror corrects an eccentric aberration which occurs due to eccentric arrangement of the plurality of mirrors.

18 Claims, 9 Drawing Sheets

FUNDUS IMAGING APPARATUS

CROSS-REFERENCE TO RELATED APPLICATION

This application claims priority from Japanese Patent Application No. 2017-069318 filed on Mar. 30, 2017, the entire subject-matter of which is incorporated herein by reference.

TECHNICAL FIELD

The present invention relates to a fundus imaging device.

BACKGROUND

The related art discloses a fundus imaging device that obtains an image of a fundus by scanning the fundus of an examinee's eye with light using an optical scanner. For example, a scanning laser ophthalmoscope (SLO) obtains a front image of a fundus as the result of scanning the fundus with light.

The capturing of a wide-range image of a fundus using such a fundus imaging device is tried (for example, refer to JP-A-2014-138904).

However, it is susceptible to improvement in an optical system of a device that captures a wide-range image of a fundus with scanning. For example, a difference in aberration between scan positions is likely to affect an image. It is considered that as disclosed in JP-A-2014-138904, if an objective optical system for widening the angle of a scanning range is formed of a lens system, the reflection of light from the surface of a lens may affect an image.

SUMMARY

A technical object of this disclosure is to provide a fundus imaging device with a new optical system which is capable of capturing a good wide-range image of a fundus.

Means for Solving the Problem (1) A fundus imaging device including:
a scanning optical system that includes an optical scanner configured to change a travelling direction of light from a light source to scan a fundus of an examinee's eye with the light; and
an objective optical system that is disposed between the optical scanner and the examinee's eye, and is configured to guide the light from the optical scanner to the fundus,
in which the fundus imaging device forms an image of the fundus based on fundus reflected light being the light reflected from the fundus,
the objective optical system includes:
a first mirror configured to reflect the light from the optical scanner, and to form a first turning point around which the light turns in correspondence with an operation of the optical scanner; and
a second mirror configured to further reflect the light reflected by the first mirror, and to form a second turning point around which the light emitted to the examinee's eye turns, and
at least one of the first mirror and the second mirror has a mirror surface being a free-form surface or an odd-order aspherical surface.

(2) The fundus imaging device as set forth in (1),
in which at least one of the first mirror and the second mirror has a mirror surface being an odd-order aspherical surface mirror.

(3) The fundus imaging device as set forth in (1),
in which a swing angle of light incident to the first mirror is smaller than a swing angle of the light at the second turning point.

(4) The fundus imaging device as set forth in (1),
in which one of which power is smaller power, out of the first mirror and the second mirror, has a mirror surface being the free-form surface or the odd-order aspherical surface.

(5) The fundus imaging device as set forth in (1) further including:
a third mirror that is disposed between the optical scanner and the first mirror, and is configured to correct an eccentric aberration in the objective optical system.

(6) The fundus imaging device as set forth in (5),
in which the third mirror has smaller power compared with the first mirror and the second mirror.

(7) The fundus imaging device as set forth in (1),
in which the free-form surface or the odd-order aspherical surface has a base surface which is a quadric surface satisfying a conjugate relationship between the optical scanner and an anterior ocular segment of the examinee's eye.

(8) The fundus imaging device as set forth in (7),
in which at least one of focal points of the quadric surface being the base surface of the free-form surface or the odd-order aspherical surface coincides with the first turning point.

(9) The fundus imaging device as set forth in (1), further including:
an optical member configured to correct an inclination of an image plane which occurs as the fundus reflected light is reflected by each mirror of the objective optical system.

(10) The fundus imaging device as set forth in (9), further including:
a correction mirror system configured to correct the inclination of the image plane, as the optical member,
in which the correction mirror system is disposed between the optical scanner and a third mirror disposed between the optical scanner and the first mirror, and
the third mirror is configured to correct an eccentric aberration in the objective optical system.

(11) The fundus imaging device as set forth in (9),
in which the scanning optical system includes a line sensor or an area sensor as a detector configured to receive the fundus reflected light, and a line-scanning SLO optical system configured to scan the fundus with line-shaped light fluxes using the optical scanner, and
the optical member is the detector disposed inclined with respect to an optical axis.

(12) The fundus imaging device as set forth in (11),
in which the detector is disposed inclined to have a Scheimpflug relationship with the fundus and the objective optical system.

(13) The fundus imaging device as set forth in (5),
in which the first mirror turns the light incident to the second mirror from the first turning point around the first turning point at a larger swing angle than a swing angle of the light incident to the first mirror from the third mirror.

(14) The fundus imaging device as set forth in (13),
in which the first mirror forms the first turning point at a focal point of the first mirror, and
the second mirror has two focal points, and is configured that the first turning point is positioned at one focal point of the second mirror to form the second turning point at the other focal point of the second mirror.

(15) The fundus imaging device as set forth in (1),
in which the first mirror corrects asymmetric distortion of an image plane which occurs due to the second mirror.

(16) The fundus imaging device as set forth in (1),
in which the first mirror has the strongest power in the objective optical system.

(17) The fundus imaging device as set forth in (1),
in which the scanning optical system includes:
an SLO optical system that includes a first optical scanner configured to scan light from a first light source, and obtains a front image of the fundus using light from the first light source;
an OCT optical system that includes a second optical scanner configured to scan measurement light from a second light source, and obtains a tomographic image of the examinee's eye using optical interferometry; and
an optical path coupling member configured to couple an optical path of the SLO optical system and an optical path of the OCT optical system between the first optical scanner and the first mirror and between the second optical scanner and the first mirror.

(18) The fundus imaging device as set forth in (17),
in which the SLO optical system and the OCT optical system are telecentric on an object side.

DETAILED DESCRIPTION

Hereinafter, a typical embodiment of this disclosure will be described with reference to the accompanying drawings.

First, an overview of a fundus imaging device (hereinafter, is abbreviated as an "imaging device") of this disclosure will be described with reference to FIGS. 1 and 2. An imaging device 100 obtains an image of a fundus by scanning the fundus of an examinee's eye E with light. An image of a fundus may be a front image or may be a tomographic image. The scanning range of the imaging device 100 of this disclosure when scanning a fundus with light may be a wide range. For example, a full angle range of 100 degree or greater may be scanned with light, and an image of this scanning range may be obtained.

Figure 1:
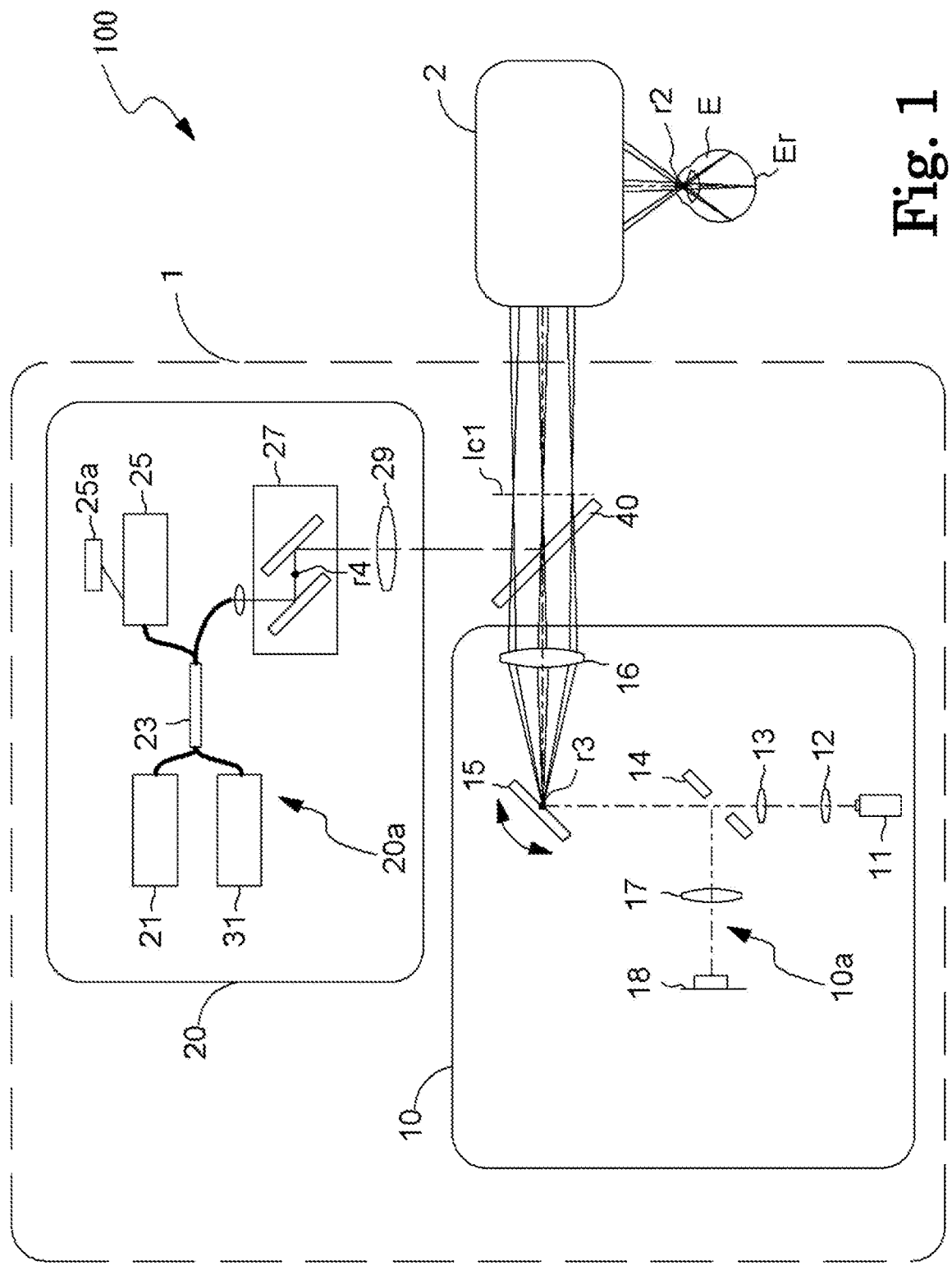
FIG. 1 is a view illustrating a schematic configuration of optical systems of a fundus imaging device of an embodiment.

As illustrated in FIG. 1, the imaging device 100 includes a scanning optical system 1 and an objective optical system 2. The imaging device 100 includes light receiving optical systems 10a and 20a. The scanning optical system 1 includes optical scanners 15 and 27 which change the travelling direction of light so as to scan a fundus Er with light from a light source. The objective optical system 2 is disposed between the scanning optical system 1 (more specifically, the optical scanners 15 and 27) and the examinee's eye E. The objective optical system 2 is used to guide light from the optical scanners 15 and 27 to the fundus Er. The light guided to the fundus Er by the objective optical system 2 is reflected and scattered by the fundus Er, and thus is emitted from a pupil. The light emitted from the pupil is received by respective detectors 18 and 31 of the light receiving optical systems 10a and 20a. As a result, images of the fundus are formed based on received light signals output from the detectors 18 and 31. For example, the detectors 18 and 31 may be provided in the scanning optical system 1.

The scanning optical system 1 may include one of an SLO optical system 10 and an OCT optical system 20. As illustrated in FIG. 1, the scanning optical system 1 may include both the SLO optical system 10 and the OCT optical system 20. The SLO optical system 10 includes the optical scanner 15, and is used to obtain a front image of the fundus Er. The SLO optical system 10 may be a line-scanning SLO optical system or a point-scanning SLO optical system. The line-scanning SLO optical system scans the fundus Er with line-shaped light fluxes in at least one direction using the optical scanner 15. The point-scanning SLO optical system two-dimensionally scans the fundus Er with dot-shaped light fluxes using the optical scanner 15. The OCT optical system 20 includes the optical scanner 27, and non-invasively obtains a tomographic image of the fundus Er via optical interferometry by scanning the fundus Er with measurement light using the optical scanner 27. In the embodiment, the optical scanners 15 and 27 and an anterior ocular segment (preferably the pupil) of the examinee's eye E have a conjugate relationship in position with respect to the objective optical system 2.

In this disclosure, "conjugation" is not necessarily limited to a perfectly conjugate relationship. In this disclosure, in addition to representing a perfectly conjugate relationship, a "conjugate" relationship may represent a positional relationship deviating from the perfectly conjugate relationship in an allowable accuracy range.

The SLO optical system 10 or the OCT optical system 20 may include two optical scanners of which scan directions are different from each other. In a case where the two optical scanners two-dimensionally scan the light, at least one of those two optical scanners may be disposed at a pupil conjugate position. In a case where the pupil conjugate positions are relayed by a relay optical system and formed at two or more locations, each of the two scanners may be disposed at each of two different pupil conjugate positions.

As illustrated in FIG. 1, in the configuration in which the scanning optical system 1 includes both the SLO optical system 10 and the OCT optical system 20, the scanning optical system 1 may include an optical path coupling member 40. The optical path coupling member 40 couples optical paths of the SLO optical system 10 and optical paths of the OCT optical system 20. In a case where the wavelength of light emitted from a light source 11 of the SLO optical system 10 is different from the wavelength of light emitted from a light source 21 of the OCT optical system 20, the optical path coupling member 40 is preferred to be a dichroic mirror, which wavelength-selectively couples optical paths together. The optical path coupling member 40 may be other optical path coupling members such as a half mirror. In FIG. 1, the optical path coupling member 40 couples the respective optical paths of the SLO optical system 10 and the OCT optical system 20 between the optical scanners of the optical systems and the objective optical system 2. As such, in the embodiment, the optical scanners are respectively provided in the SLO optical system 10 and the OCT optical system 20. As a result, it is possible to easily obtain a tomographic image at an arbitrary position in parallel with acquiring a front image.

The light receiving optical system 10a receives fundus reflected light of irradiated light from the SLO optical system 10 via a detector 18. Fundus reflected light of irradiated light (measurement light) from the OCT optical system 20 is combined with reference light, and then is received by the detector 31 of the light receiving optical system 20a.

The objective optical system 2 forms a turning point (second turning point in the embodiment) in the anterior ocular segment (for example, pupillary zone) of the examinee's eye E around which light through the optical scanners 15 and 27 turns in correspondence with the operation of the optical scanners 15 and 27. As illustrated in FIG. 2, the objective optical system 2 may be a mirror system. In this case, the objective optical system 2 may not include lens elements. In a mirror system that does not include lens elements, it is possible to prevent an image of the fundus from being affected by noise (for example, causing flare in a front image) caused by the objective optical system 2.

The objective optical system 2 includes at least a first mirror 50 and a second mirror 60. As illustrated in FIG. 2 in addition to the first mirror 50 and the second mirror 60, the objective optical system 2 of the embodiment may include optical members such as a mirror.

In the embodiment, the first mirror 50 is disposed between the scanning optical system 1 and the second mirror 60. Light from the optical scanners 15 and 27 is incident to the first mirror 50, and the first mirror 50 relays the incident light to the second mirror 60.

Figure 2:
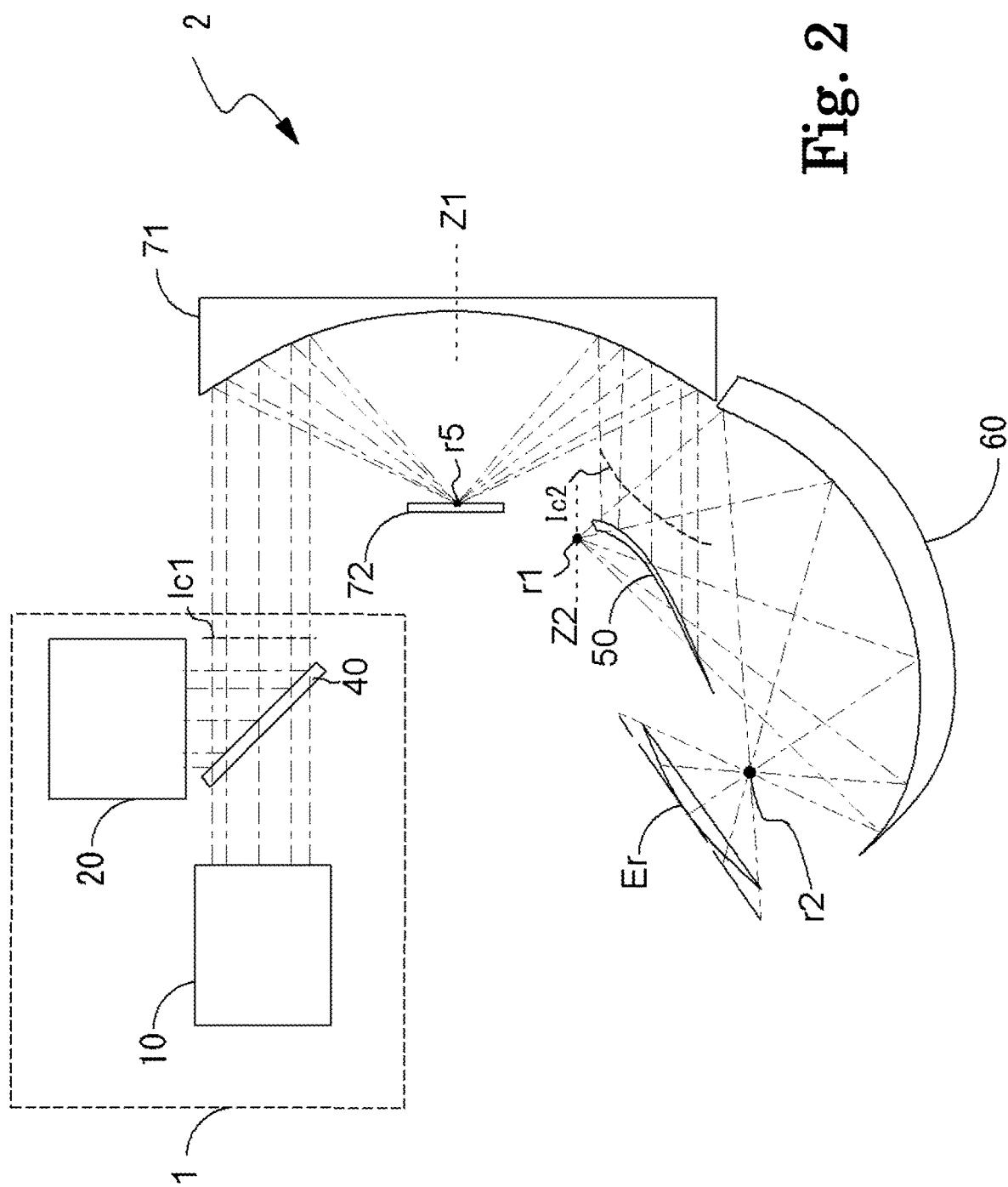
FIG. 2 is a view illustrating an objective optical system of a first example.

In the embodiment, the first mirror 50 reflects light from the optical scanners 15 and 27, and thus forms a first turning point (represented by reference sign r1 in FIG. 2). The light (specifically, light reflected by the first mirror) turns in correspondence with the operation of the optical scanners 15 and 27 around the first turning point r1.

In the embodiment, the first mirror 50 is a mirror having a focal point, and has positive power or negative power. The first mirror 50 forms the first turning point at the focal point of the first mirror 50. Furthermore, "power" of the mirror means a force for bending the light.

The first mirror 50 may be an aspherical mirror, the mirror surface of which is a quadric surface. The "aspherical mirror" is defined in the description stated below as a mirror of which a mirror surface is a curved surface formed along a trajectory that is obtained by rotating a curve around a symmetrical axis unless otherwise specified. A quadric surface is formed along a trajectory that is obtained by rotating a quadratic curve (also referred to as a conic section) around a symmetrical axis. An aspherical mirror as the first mirror 50 having a quadric surface may be at least any one of a paraboloidal mirror, a hyperboloidal mirror, and an ellipsoidal mirror, but a mirror surface of the first mirror 50 is not limited thereto. For example, the first mirror 50 may be a spherical mirror.

Furthermore, the first mirror 50 may be an odd-order aspherical mirror of which a mirror surface is an odd-order aspherical surface. In this case, a function representing a mirror surface shape of the first mirror 50 has an odd-order aspherical coefficient.

Moreover, the first mirror 50 may be a free-form mirror of which a mirror surface is a free-form surface. In this case, the free-form mirror may be an x-y polynomial mirror. Furthermore, in this disclosure, so-called asymmetric aspherical mirror is considered as one of the free-form mirror.

The first mirror 50 of the embodiment is formed of one mirror unless otherwise specified, but not limited thereto. Alternatively, the first mirror 50 formed of one mirror may be replaced with a combination of multiple mirrors.

The second mirror 60 has positive power. The second mirror 60 further reflects the light reflected by the first mirror 50, and thus forms the second turning point around which light to be emitted from the objective optical system 2 to the examinee's eye E turns.

In the embodiment, the second mirror 60 has two focal points r1 and r2. The examinee's eye E is disposed at the focal point r2. More specifically, the anterior ocular segment (for example, the position of the pupil) is disposed at the position of the focal point r2. The first mirror 50 and the second mirror 60 are disposed such that the first turning point formed by the first mirror 50 coincides with the focal point r1 of the second mirror 60. In the embodiment, as a result, the second turning point r2, around which light traveling from the objective optical system 2 toward the fundus Er turns, is formed at the focal point r2.

Figure 3:
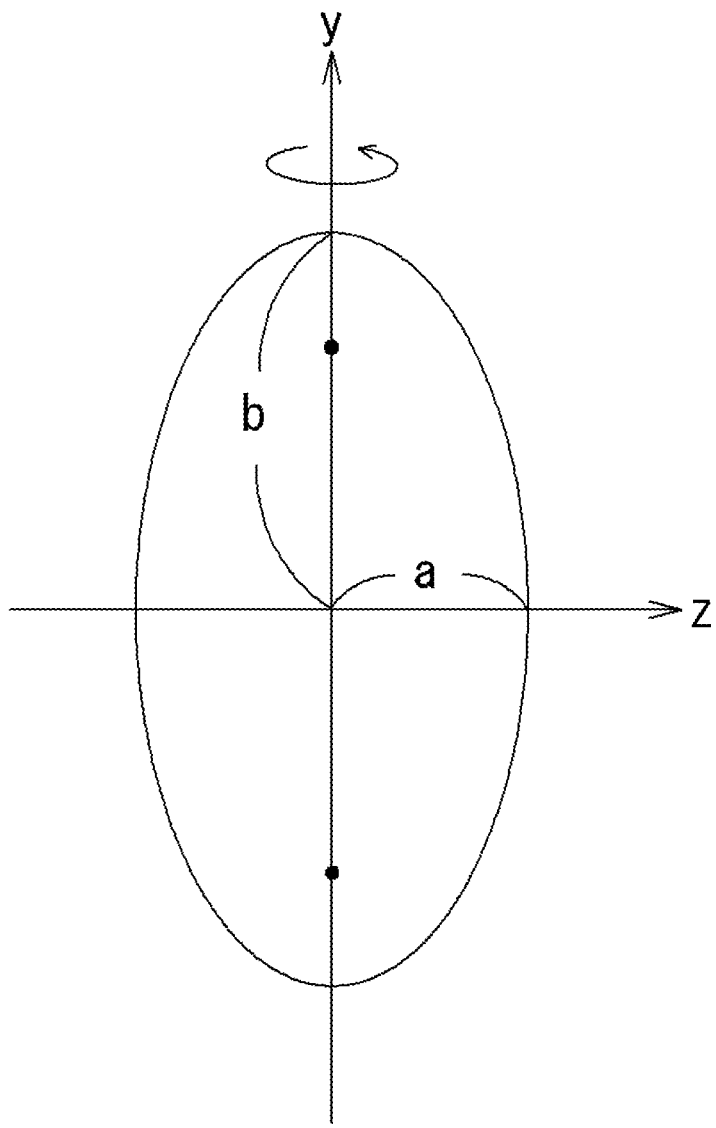
FIG. 3 is a view illustrating an ellipsoidal mirror shown in FIG. 2.

The second mirror 60 illustrated in FIG. 2 is a spheroidal mirror (ellipsoidal mirror). The spheroidal mirror may be a toroidal mirror illustrated in FIG. 3, i.e., a mirror surface may be an ellipsoidal surface formed by rotating an oblate ellipsoid with a major axis 2a in the y direction and a minor axis 2b in the z direction around the major axis. In this case, light, which passes through the focal point r1 and is reflected by the mirror surface of the spheroidal mirror, always passes through the focal point r2. Accordingly, light with which the examinee's eye E is irradiated is disposed at the focal point r2 is unlikely to causing vignetting in the pupil. Furthermore, in a case of the spheroidal mirror, the focal point r2 is formed on a reflection side, thus light is easily incident at a steep angle with respect to a visual axis. As a result, it is possible to capture a wide angle image of the fundus.

A curved mirror other than a spheroidal mirror may be adopted as the second mirror 60. The curved mirror may be an aspherical mirror (as a specific example, a paraboloidal mirror, a pair of hyperboloidal mirrors, or the like) having a quadric mirror surface similar to a spherical mirror. The curved mirror may be an aspherical mirror having a shape other than a quadric mirror surface. For example, the second mirror 60 may be an odd-order aspherical mirror of which a mirror surface is an odd-order aspherical surface. Moreover, the second mirror 60 may have a free-form mirror of which a mirror surface is a free-form surface. The odd-order aspherical surface or the free-form surface may have a spheroidal mirror (toroidal mirror) as a base surface. The base surface will be described later in detail.

The second mirror 60 of the embodiment is formed of one mirror. Alternatively, the second mirror 60 formed of one mirror may be replaced with a combination of multiple mirrors. The shape and the size of the second mirror 60 are suitably set according to the angle of a captured image. For example, in the embodiment, the second mirror 60 may have such a shape and a size that it is possible to capture an image of a full angle of approximately 120°.

Due to the configuration of the mirrors, the objective optical system 2 of the embodiment further decreases the swing angle of light which is incident to the first mirror 50 through the optical scanners 15 and 22, compared to a swing angle with respect to the second turning point r2. The first mirror 50 may have larger power than that of the second mirror 60.

In the embodiment, one or both of the first mirror 50 and the second mirror 60 cause the angle of an imaging range to be widened to a desired image angle. As in the example illustrated in FIG. 2, at least the first mirror 50 further increases the swing angle of light travelling from the first turning point r1 toward the second mirror 60 compared to the swing angle of light incident to the first mirror 50 through the optical scanners 15 and 27 (more specifically, the swing angle of light incident to the objective optical system 2). As a result, an image angle may be widened. It is possible to obtain the shape and the disposition of the second mirror 60 via simulation or the like using a beam tracing method.

Each of the first mirror 50 and the second mirror 60 has an eccentric reflective surface (in other words, the objective optical system 2 is an eccentric reflective optical system). Therefore, an eccentric aberration occurs in addition to a rotational symmetrical aberration. On the contrary, by employing the free-form surface or the odd-order aspherical surface, it is possible to correct the eccentric aberration, which cannot be corrected by a general spherical or aspherical surface.

For example, a third mirror that is an odd-order aspherical mirror or a free-form mirror may be provided in the imaging device 100, separately from the first mirror 50 and the second mirror 60. That is, one of the scanning optical system 1 and the objective optical system 2 may be provided with the third mirror. The third mirror may be disposed between, for example, the first mirror 50 and the optical scanners 15 and 27. The third mirror corrects the eccentric aberration which occurs due to the objective optical system 2 which is an eccentric optical system.

In this case, the odd-order aspherical mirror or the free-form mirror preferably includes a base surface that is a mirror surface having a quadric surface. That is, in an aspherical mirror having a quadric surface as the base surface of the odd-order aspherical mirror or the free-form mirror, at least one of focal points substantially coincides with a turning point (it will described later in detail). Even in a case where the points are deviated in both mirrors within a range satisfying a conjugate relationship between the anterior ocular segment and the optical scanners 15 and 22, as well as an advantageous effect of reducing the eccentric aberration, it is allowed as considered that the points in both mirrors substantially coincide each other.

However, the third mirror does not need to have the odd-order aspherical surface or the free-form surface. Even the third mirror has a quadric surface, a specified effect of reducing the eccentric aberration can be obtained. That is, a quadric mirror, that corrects the eccentric aberration which occurs due to the objective optical system 2 which is an eccentric optical system, may serve as the third mirror. For example, in FIG. 7, hyperboloidal mirrors 211 and 221 are provided between the first mirror 50 and the optical scanner as the third mirrors.

Furthermore, at least one of the first mirror 50 and the second mirror 60 may be the odd-order aspherical mirror or the free-form mirror. In this case, by the first mirror 50 or the second mirror 60, the eccentric aberration which occurs due to the objective optical system 2 may be reduced.

In a case where the odd-order aspherical mirror or the free-form mirror is employed as one of the first mirror 50 and the second mirror 60, or any one of the first mirror 50, the second mirror 60 and the third mirror, a mirror having the smallest power among those mirrors may be the odd-order aspherical mirror or the free-form mirror. As the odd-order aspherical mirror or the free-form mirror has smaller power, the degree of freedom in shape is more easily secured while suppressing the aberration. Hence, it is possible to efficiently suppress the eccentric aberration by the odd-order aspherical mirror or the free-form mirror. In particular, in a case where the third mirror is provided, it is preferable that the third mirror is the odd-order aspherical mirror or the free-form mirror, which has smaller power than that of the first mirror 50 or the second mirror 60.

Furthermore, in the embodiment, in a case where the odd-order aspherical mirror or the free-form mirror is employed as any one of the mirrors, a base surface of which does not have to be a quadric surface (aspherical surface). The base surface of the odd-order aspherical mirror or the free-form mirror may be a spherical surface or a plane surface.

If the first mirror 50 is not provided, and one of the respective optical scanners 15 and 27 of the SLO optical system 10 and the OCT optical system 20 is disposed at the focal point r1 of the second mirror 60, and light is directly guided from the optical scanner to the second mirror 60, the following problem occurs. That is, it is difficult to ensure a sufficient space between the optical scanner and the second mirror 60. It is necessary to increase the swing angle of the optical scanner so as to scan a wide range on the fundus with light. In this case, it is more difficult to suitably dispose the optical path coupling member 40 in the space between the optical scanner and the second mirror 60. The optical path coupling member 40 may have incidence angle dependence. For example, a dichroic mirror which is an example of the optical path coupling member 40 may not be able to suitably transmit or reflect light that is incident thereto at an incidence angle which significantly deviates from a design value. For this reason, even if it is possible to dispose an optical path coupling member such as a dichroic mirror between the second mirror 60 and the optical scanner disposed at the position of the focal point r1, in this case, image quality at the image angle (wide angle side) of a portion of a fundus image deteriorates. For this reason, the capturing of a wide-range image of the fundus by one or both of the SLO optical system and the OCT optical system becomes difficult.

In contrast, in the embodiment, the first mirror 50 is interposed between the optical scanners 15 and 27 and the second mirror 60. As the result of providing the first mirror 50, the objective optical system 2 causes light to turn around the first turning point r1 at a larger swing angle compared to the swing angle of light that is incident to the objective optical system 2 from the scanning optical system 1. In other words, it is possible to further decrease the swing angle of light which is incident to the first mirror 50 through the optical scanners 15 and 27, compared to the swing angle with respect to the first turning point r1. In other words, it is possible to form an area, in which the swing angle of light is smaller than the swing angle light incident to the second mirror 50, at a position closer to a light source side than to the second mirror 50. As a result, it is possible to easily ensure a space, in which the optical path coupling member 40 is disposed, in the area in which the swing angle of light is smaller than the swing angle of light incident to the second mirror 50. It is possible to reduce a problem of incidence angle dependence of the optical path coupling member 40 by disposing the optical path coupling member 40 in this area. For example, as illustrated in FIG. 1, it is possible to satisfactorily couple the optical paths of the SLO optical system 10 and the optical paths of the OCT optical system 20 by disposing the optical path coupling member 40 between the optical scanner 15 of the SLO optical system 10 and the first mirror 50 and between the optical scanner 27 of the OCT optical system 20 and the first mirror 50. As a result, it is possible to acquire a good front image and a good tomographic image.

As illustrated in FIG. 1, the SLO optical system 10 and the OCT optical system 20 may be telecentric with respect to an object side. In this case, since the incidence angle of light incident to the optical path coupling member 40 is the same regardless of scan position, it is possible to satisfactorily prevent a loss in the amount of light caused by the coupling of the optical paths, and to obtain a good image of the fundus.

As illustrated in FIG. 2, in a case where a spheroidal mirror is used as the second mirror 60, the asymmetric distortion (for example, trapezoidal distortion) of an image plane occurs due to the second mirror 60. It is considered that even if the second mirror 60 adopts a shape other than that of a spheroidal mirror, the distortion of an image plane in a mirror surface shape may occur.

The distortion of the image plane caused by the second mirror 60 is corrected by the first mirror 50. The first mirror 50 may be disposed inclined with respect to the second mirror 60 such that the distortion of the image plane is be corrected. The inclination referred to here implies that the first mirror 50 is disposed in such a way that the axis (for example, the symmetrical axis of a quadratic curve of a mirror surface of an aspherical mirror) is inclined with respect to a beam (mainly, beam passing through the optic axis of the examinee's eye E) passing through the center of optical paths between the first mirror 50 and the second mirror 60. The amount of inclination is desirably set to some extent that at least asymmetric components of the distortion of the image plane are cancelled out. That is, the amount of inclination may be adopted such that the remaining distortion of the image plane is axis-symmetric.

In the example illustrated in FIG. 2, it is considered that as the result of using a spheroidal mirror as the second mirror 60, the image plane of an intermediate image Ic2 caused by fundus reflected light is obliquely inclined with respect to the optical axis of the optical system. It is considered that even if the second mirror 60 adopts a shape other than that of a spheroidal mirror, the inclination of an image plane may occur.

In contrast, the imaging device 100 of the embodiment may be provided with an optical member that corrects an inclination of an image plane which occurs as the fundus reflected light is reflected by the first mirror 50 and the second mirror 60.

For example, an optical member which corrects the inclination of an image plane may be disposed on common optical paths of projected light optical paths along which light from the light sources 11 and 21 is guided to the examinee's eye E, and light receiving optical paths along which fundus reflected light is guided to the detectors 18 and 31. Optical members may be respectively disposed on independent optical paths of the projected light optical paths and on independent optical paths of the light receiving optical paths is reduced.

Figure 9:
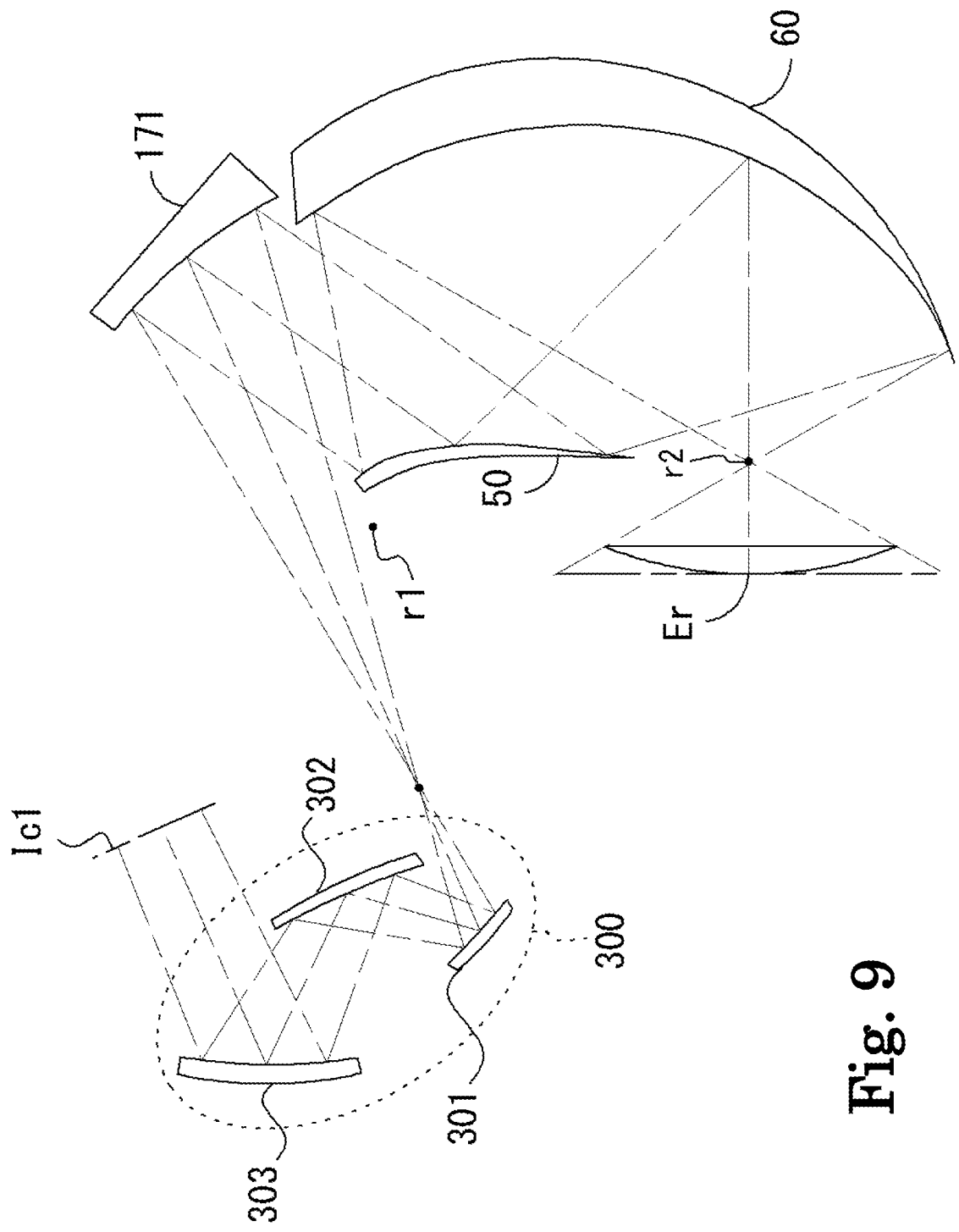
FIG. 9 is a view illustrating an optical system of a fifth example.

As a specific example in which an optical member is disposed on common optical paths, the objective optical system 2 may be provided with correction mirror systems 71, 72 and 300 which are optical members to correct the inclination of an image plane caused by fundus reflected light, between the first mirror 50 and the optical scanners 15 and 27. The correction mirror systems 71, 72 and 300 further incline an image plane so as to cancel out (reduce) the inclination of the image plane caused by the first mirror 50 and the second mirror 60 (that is, which occurs due to the objective optical system 2). As a result, as illustrated in FIGS. 2 and 9, the inclination of the image plane of an intermediate image (for example, intermediate image Ic1 in FIG. 2) formed by the fundus reflected light through the correction mirror systems 71, 72 and 300 is reduced.

Figure 8:
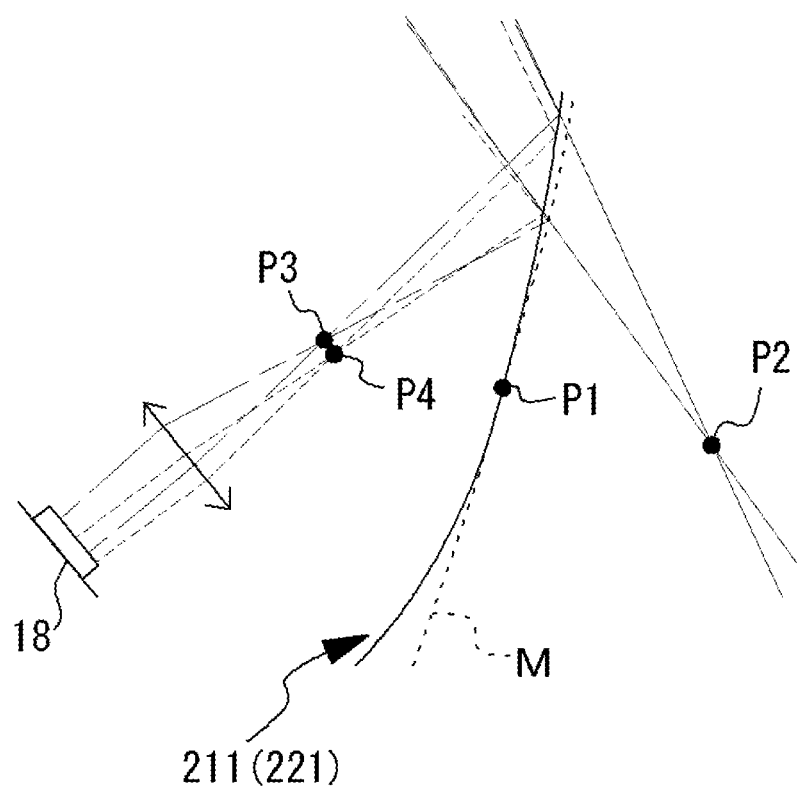
FIG. 8 is a view illustrating an enlarged view of a free-form mirror of the fourth example.

At least one mirror of the aforementioned correction mirror systems for correcting the inclination of the image plane may be the odd-order aspherical mirror or the free-form mirror. As one example, FIG. 8 shows an optical system in which the free-form mirror is employed as each of the mirrors in the correction mirror systems (it will be described later in detail).

As another specific example, a lens inclined with respect to the optical axis thereof may be disposed on the common optical paths such that the inclination of an image plane is corrected. For example, in the example illustrated in FIG. 1, scan lenses 16 and 29 may be inclinedly disposed.

In a case where optical members are respectively disposed on the independent optical paths of the projected light optical paths and on the independent optical paths of the light receiving optical paths, at least the detector 18 of the SLO optical system 10 may be used as one of the optical members. For example, in a case where the SLO optical system 10 is a line-scanning SLO optical system, a line sensor or an area sensor is used as the detector 18. In this case, it is possible to correct the inclination of an image plane by inclining the detector 18 with respect to an optical axis of the light receiving optical system 10a. The amount of inclination of the detector 18 is desirably adjusted to have a Scheimpflug relationship with the fundus Er and the objective optical system 2. Furthermore, independent optical paths of the projected light optical system 10a of the SLO optical system 10 may include an optical member such as a lens, which is disposed inclined with respect to the optical axis thereof.

In a case where the SLO optical system 10 is a point-scanning SLO optical system, an optical member (an inclinedly disposed lens, a correction mirror system, or the like) separate from the detector is desirably provided on the light receiving optical paths from the detector to the examinee's eye E. Accordingly, it is possible to prevent the confocal position of the fundus Er from moving in correspondence with a change in the scan position of the optical scanner 15 by preventing the inclination of an image plane. As a result, it is possible to form a stationary conjugate point of the fundus between the optical member and the detector 18. For this reason, it is possible to dispose an aperture for removing undesired light at a stationary confocal position, and to obtain a good front image.

First Example

The imaging device 100 of a first example will be described with reference to FIG. 1. The imaging device 100 of the first example includes the scanning optical system 1 illustrated in FIG. 1 and the objective optical system 2 illustrated in FIG. 2. The scanning optical system 1 includes the SLO optical system 10; the OCT optical system 20; and a dichroic mirror (optical path coupling member in the first example) 40.

<SLO Optical System>

First, the SLO optical system 10 will be described. The SLO optical system 10 includes mainly the optical scanner 15 that two-dimensionally scans the fundus with light (illumination light) emitted from a light source; the detector 18; and the light receiving optical system 10a that receives fundus reflected light (of illumination light), which passes through a confocal point of the fundus Er, via the detector. In the first example, a line-scan type SLO optical system is used as the SLO optical system 10, and a line sensor is used as the detector 18. In this case, in addition to the optical scanner 15 and the detector 18, the SLO optical system 10 may include the light source 11; a collimating lens 12; a columnar lens 13; an aperture mirror 14; the scan lens 16; and a condenser lens 17. The light receiving optical system 10a of the SLO optical system 10 of the first example is formed of the optical scanners 15, the scan lens 16, the condenser lens 17, and the line sensor (detector) 18 among these elements.

In the first example, the light source 11 emits light (for example, laser beams) having infrared wavelengths. An LED light source, an SLD light source, or the like may be used as the light source 11. Light from the light source 11 is collimated by the collimating lens 12, and then is concentrated by the columnar lens 13. Thereafter, the light passes through an aperture of the aperture mirror 14, and is guided to the optical scanner 15. Light emitted from the light source 11 is not necessarily limited to infrared light. For example, light from the light source 11 may be white light, or may be combined light which is a combination of two or more colors (for example, red, blue, and green) of light.

In the first example, a galvanometer mirror may be used as the optical scanner 15. The optical scanner 15 is not necessarily limited to a galvanometer mirror. A galvanometer mirror may be replaced with any one of other optical scanners (a resonant mirror, a polygon mirror, and the like) which operates a reflective mirror, an acousto-optical device, and the like. The optical scanner 15 is disposed at a conjugate position with respect to the pupil of the examinee's eye E.

The scan lens 16 turns light through the optical scanner 15 into beams (that is, telecentric beams) parallel to an optical axis L1 of the scanning optical system 1. That is, in the first example, the scan lens 16 is disposed such that a focal point of the scan lens 16 coincides with that of the optical scanner 15 (turning point r3 of the optical scanner 15). Accordingly, the SLO optical system 10 of the first example is telecentric with respect to an object side. Light passing through the scan lens 16 further passes through the dichroic mirror 40, and is incident to the objective optical system 2. In the first example, the dichroic mirror 40 has spectral characteristics by which the dichroic mirror 40 transmits light from the SLO optical system 10, and reflects light from the OCT optical system 20. To be telecentric with respect to an object side implies a state of being telecentric with respect to the examinee's eye E side when beams viewed from a light source 11 or 22 side.

Light from the SLO optical system 10 is guided to the fundus Er by the objective optical system 2, and then is scattered and reflected by the fundus Er. As a result, fundus reflected light is emitted from the pupil, and travels along optical paths opposite to those when light is projected. The fundus reflected light is emitted from the objective optical system 2 toward the scanning optical system 1, passes through the dichroic mirror 40, and is incident to the light receiving optical system 10a of the SLO optical system 10. In the light receiving optical system 10a, the fundus reflected light passes through the scan lens 16, is reflected by the optical scanner 15, and travels toward the aperture mirror 14. Thereafter, the fundus reflected light reflected by the aperture mirror 14 is concentrated by the condenser lens 17, and is received by the detector 18. In the embodiment, a front image of the fundus is formed based on signals which are output from the detector 18 based on one frame of light scanning performed by the optical scanner 15.

<OCT Optical System>

Hereinafter, the OCT optical system 20 will be described. The OCT optical system 20 may include the light source 21; an optical splitter (coupler in the example illustrated in FIG. 1) 23; the optical scanner 27; and the detector 31. The OCT optical system 20 may further include the scan lens 29 and a reference optical system 25.

Fourier domain types such as a swept source-OCT (SS-OCT) type and a spectral domain-OCT (SD-OCT) type may be used as the OCT optical system 20. Hereinafter, as an example, a swept source-OCT (SS-OCT) type used as the OCT optical system 20 will be described.

The light source 21 is a variable wavelength light source (wavelength scanning light source) that changes an emitted wavelength at a high speed. The light source 21 changes the wavelength of emitted light. The detector 31 may be a balanced detector formed of light receiving elements.

The OCT optical system 20 splits light emitted from the light source 21 into measurement light and referent light via the coupler (splitter) 23.

The OCT optical system 20 guides the measurement light to the objective optical system 2 via the optical scanner 27. The OCT optical system 20 guides the reference light to the reference optical system 25. The optical scanner 27 scans the fundus Er with the measurement light in an XY direction (traverse direction). The optical scanner 27 is formed of two galvanometer mirrors. The angle of reflection may be arbitrarily adjusted by a drive mechanism (not illustrated). Other optical scanners (a resonant mirror, a polygon mirror, an MEMS mirror and the like) which operates a reflective mirror, an acousto-optical device, and the like may be used instead of galvanometer mirrors.

The scan lens 29 turns light through the optical scanner 27 into beams (that is, telecentric beams) parallel to the optical axis of the scanning optical system 1. That is, in the first example, the scan lens 29 is disposed such that a focal point of the scan lens 29 coincides with that of the optical scanner 27 (for example, intermediate point r4 between an X-scan optical scanner and a Y-scan optical scanner). Accordingly, the OCT optical system 20 of the embodiment is telecentric with respect to an object side. Light passing through the scan lens 29 is reflected by the dichroic mirror 40, and then is incident to the objective optical system 2.

Similar to light from the SLO optical system 10, the light from the OCT optical system 20 is guided to the fundus Er by the objective optical system 2, and then is scattered and reflected by the fundus. As a result, fundus reflected light of the measurement light travels through the objective optical system 2 along optical paths opposite to those when light is projected, and is emitted toward the scanning optical system 1. The fundus reflected light of the measurement light is reflected by the dichroic mirror 40, and is incident to a detective optical system 20a of the OCT optical system 20 (light receiving optical system of the OCT optical systems 20). That is, the fundus reflected light passes through the scan lens 29, and is incident to the coupler (splitter) 23 through the optical scanner 27. Thereafter, the reflected light of the measurement light is combined with reference light by the optical splitter (coupler) 23, and interferes therewith.

The reference optical system 25 generates reference light that is to be combined with reflected light acquired due to reflection of measurement light by the fundus Er. The reference optical system 25 may be a Michelson type, or may be a Mach-Zehnder type. In FIG. 1, the reference optical system 25 includes a reflective optical system (for example, a reference mirror), and guides reference light to the detector 31 by reflecting light from the coupler 23 via the reflective optical system. As another example, the reference optical system 25 may include a transmissive optical system (for example, an optical fiber), and may guide light from the coupler 23 to the detector 31 by transmitting the light instead of returning the light.

The imaging device 100 moves at least a portion of the optical members disposed in the OCT optical system 20 in an optical axial direction so as to adjust an optical path length difference between measurement light and reference light. For example, the reference optical system 25 includes a configuration element that adjusts an optical path length difference between measurement light and reference light by moving an optical member (for example, a reference mirror not illustrated) on reference optical paths. The reference mirror is moved in the optical axial direction by driving a drive mechanism 25a. A configuration element for changing an optical path length difference may be disposed on optical paths of measurement light. That is, the optical path length difference between measurement light and reference light may be adjusted by changing the optical path length of measurement light.

The detector 31 receives interference signal light which is a combination of measurement light and reference light. The detector 31 detects interference signal light. If an emitted wavelength from the light source 21 is changed, the detector 31 receives interference signal light in correspondence with the change, and as a result, receives the interference signal light as spectral interference signal light. Depth profiles (may be referred to as A scan or OCT data) at one point on the fundus are formed based on spectral interference signals output from the detector 31. The depth profiles are a reflection intensity distribution of measurement light in a depth direction of the fundus. Two-dimension OCT data (a tomographic image of the fundus, OCT angiography, or the like) is formed by aligning the depth profiles (OCT data).

<Objective Optical System>

Hereinafter, the objective optical system 2 of the first example will be described with reference to FIG. 2. In the example illustrated in FIG. 2, the second mirror 60 is one spheroidal mirror. The second mirror 60 has the two focal points r1 and r2. The examinee's eye E is disposed at the focal point r2 of these.

In the first example, the first mirror 50 is a paraboloidal mirror. In the first example, the first mirror 50 and the second mirror 60 are disposed such that the focal point of the first mirror 50 which is a paraboloidal mirror coincides with one (the focal point r1) of the two focal points of the second mirror 60 which is a spheroidal mirror. The remaining one (the focal point r2) of the two focal points of the second mirror 60 is disposed on the anterior ocular segment of the examinee's eye E. In this case, a convex surface of the first mirror 50 and a concave surface of the second mirror 60 are used as reflective surfaces. The paraboloidal mirror converts light, which is incident thereto while being parallel to a symmetrical axis Z2, into light that is emitted from the focal point r1 by appearance. The first mirror 50 concentrates the light, which is emitted from the focal point r1, to the focal point r2. For this reason, in the first example, light from the SLO optical system 10 and the OCT optical system 20 which are telecentric with respect to the object side is incident to the first mirror 50 while being parallel to the symmetrical axis of the first mirror 50. Therefore, light from the SLO optical system 10 and light from the OCT optical system 20 are capable of turning around the focal point r2 that is a turning point positioned on the anterior ocular segment of the examinee's eye E. Since the first mirror 50 and the second mirror 60 of the objective optical system 2 have the aforementioned shapes and are disposed as described above, it is possible to decrease the swing angle of light incident to the first mirror 50 through the optical scanners 15 and 22, and to scan a wide range on the fundus with light.

The first mirror 50 formed of a paraboloidal mirror has been described, and is one example of specific examples of an aspherical mirror that widens an imaging angle. An aspherical mirror other than a paraboloidal mirror may be adopted as the first mirror 50.

In the first example, in addition to the first mirror 50 and the second mirror 60, the correction mirror systems 71 and 72 are provided in the objective optical system 2. In the first example, the correction mirror systems 71 and 72 are respectively formed of a paraboloidal mirror and a plane mirror, and are also referred to as a paraboloidal mirror 71 and a plane mirror 72. The inclination of an image plane occurs as the fundus reflected light is reflected by the first mirror 50 and the second mirror 60 which is a spheroidal mirror. The correction mirror systems 71 and 72 correct this inclination of the image plane. In the first example, light from the SLO optical system 10 and the OCT optical system 20 which are telecentric on the object side is incident to the first mirror 50 while being parallel to the symmetrical axis z2.

In the first example, the paraboloidal mirror 71 has a concave surface that is formed symmetrical with respect to a symmetrical axis z1. Light from the scanning optical system 1 is incident to the correction mirror system 71 while being parallel to the symmetrical axis z1. The plane mirror 72 is disposed at the position of a focal point r5 of the paraboloidal mirror 71 while confronting the paraboloidal mirror 71. If light from the scanning optical system 1 is incident to the correction mirror systems 71 and 72, the light is reflected by the paraboloidal mirror 71, the plane mirror 72 (that is, the focal point r5 of the paraboloidal mirror), and the paraboloidal mirror 71 in the listed sequence, and is emitted from the paraboloidal mirror 71 while being parallel to the symmetrical axis z1. For this reason, light fluxes are telecentric on both of front and rear of a correction mirror system 71 side and a correction mirror system 72 side. An image plane is inclined by the reflection of the correction mirror systems 71 and 72 (refer to the intermediate image Ic2 in FIG. 2). The image plane is inclined by the correction mirror systems 71 and 72 in such a way as to cancel out the inclination of an image plane which occurs due to the first mirror 50 and the second mirror 60. As illustrated in FIG. 2, in a case where the inclination occurring due to the first mirror 50 and the second mirror 60 is non-linear, the correction mirror systems 71 and 72 desirably cancel out at least non-linear components of the inclination.

The first mirror 50 of the first example is a convex mirror, the convex surface of which faces the paraboloidal mirror 71 and the second mirror 60. That is, the first mirror 50 has negative power. The first mirror 50 is disposed eccentric (off-axis) with respect to the paraboloidal mirror 71. That is, the symmetrical axis z2, which is the symmetrical axis (that is, the object axis of a paraboloidal surface) of the mirror surface of the first mirror 50, is parallel to the symmetrical axis z1 of the paraboloidal mirror 71 while being spaced from the symmetrical axis z1. For this reason, the first mirror 50 is irradiated with beams from the paraboloidal mirror 71 which are parallel to the symmetrical axis z2. The first mirror 50 is disposed such that the focal point of the first mirror 50 coincides with the focal point r1 of the two focal points r1 and r2 of the second mirror 60 which is a spheroidal mirror. For this reason, in a case where a position on the first mirror 50 is irradiated with light from the paraboloidal mirror 71, the light is reflected along a straight line through which the irradiation position is connected to the focal point r1. That is, light from the first mirror 50 toward the second mirror 60 turns around the focal point r1 of the second mirror 60, which is a spheroidal mirror, in correspondence with the driving of the optical scanner 15 (or the optical scanner 27). In other words, a turning point of light travelling toward the second mirror 60 through the optical scanner 15 (or the optical scanner 27) is formed at the focal point r1 by the first mirror 50. In the first example, since light is reflected by the mirror surface of the first mirror 50, the swing angle of light from the first turning point r1 toward the second mirror 60 is further increased compared to the swing angle of light incident to the first mirror 50 from the scanning optical system 1. For this reason, in the first example, the swing angle of light incident to the first mirror 50 is further decreased compared to that of light incident to the second mirror 60. As an example, as illustrated in FIG. 1, telecentric light can be incident. In this case, it is considered that the swing angle is equal to zero.

Due to general characteristics of a spheroidal mirror, that is, the second mirror 60, light, which passes through the focal point r1 and is reflected by the mirror surface of the spheroidal mirror, is guided to the focal point r2. For this reason, a turning point (the second turning point) of light reflected by the second mirror 60 is formed at the focal point r2 (that is, the position of the anterior ocular segment of the examinee's eye E). The swing angle of light around the turning point (the focal point r2) is determined by a swing angle with respect to the focal point r1 and the shape of the mirror surface of the second mirror 60. The second mirror 60 may have a shape that further increases the swing angle with respect to the focal point r2 compared to the swing angle with respect to the focal point r1. The present invention is not necessarily limited to that configuration.

As such, in the first example, telecentric (swing angle=0) light is incident to the objective optical system 2 (more specifically, the paraboloidal mirror 71) from the scanning optical system 1, and thus, it is possible to capture a wide-range image of the fundus Er. In the first example, the optical path coupling member 40 (the dichroic mirror 40), which couples the respective optical paths of the SLO optical system 10 and the OCT optical system 20 together, is disposed at a location in which the SLO optical system 10 and the OCT optical system 20 are telecentric. As a result, it is possible to obtain a good front image and a good tomographic image at a wide image angle.

Since the second mirror 60 is a spheroidal mirror, the asymmetric distortion (for example, trapezoidal distortion) of an image plane of fundus reflected light. In contrast, in the example, the first mirror 50 is disposed inclined with respect to the second mirror 60, and thus, the distortion of an image plane is prevented. That is, the first mirror 50 is disposed inclined with respect to a beam passing through the center of the optical paths between the first mirror 50 and the second mirror 60. The amount of correction of distortion of the image plane is changed in correspondence with the amount of inclination of the first mirror 50. The amount of inclination of the first mirror 50 may be set such that the remaining distortion of the image plane is axis-symmetric.

<Control System>

Figure 4:
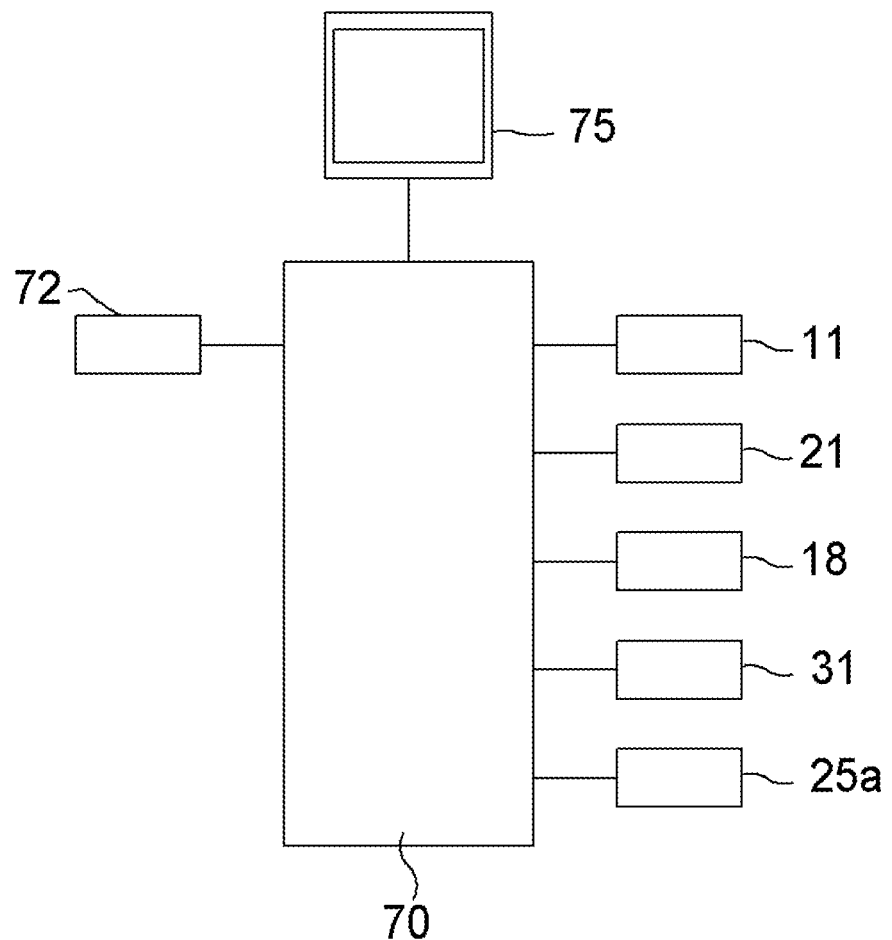
FIG. 4 is a block diagram illustrating an electrical configuration of a fundus imaging device of the first example.

Hereinafter, a control system of the imaging device 100 will be described with reference to FIG. 4. A control unit 70 is a processor (for example, a CPU) that controls the entirety of the imaging device 100.

In the first example, the control unit 70 is electrically connected to a memory 72, a monitor 75 and the like. The control unit 70 is electrically connected to the light sources 11 and 21, the optical scanners 15 and 27, the detectors 18 and 31, the drive mechanism 25a, and the like.

The memory 72 stores various control programs and fixed data. The memory 72 may store images captures by the imaging device 100, temporary data, and the like.

In the embodiment, the control unit 70 also serves as an image processing unit. For example, received light signals from the detectors 18 and 31 are input to the control unit 70. The control unit 70 forms a front image of the fundus Er based on the signals from the detector 18. The control unit 70 forms a tomographic image of the fundus Er based on the signals from the detector 31. The control unit 70 may acquire both of a front image and a tomographic image by concurrently and independently driving light from the light source 11 and light from the light source 21 via the optical scanners 15 and 27. The front image and the tomographic image concurrently obtained may be concurrently displayed on the monitor 75 in the form of a moving image. In the first example, the optical scanner 15 of the SLO optical system 10 is provided independently from the optical scanner 27 of the OCT optical system 20, and thus, the control unit 70 may acquire a front image and a tomographic image at different frame rates.

Second Example

Figure 5:
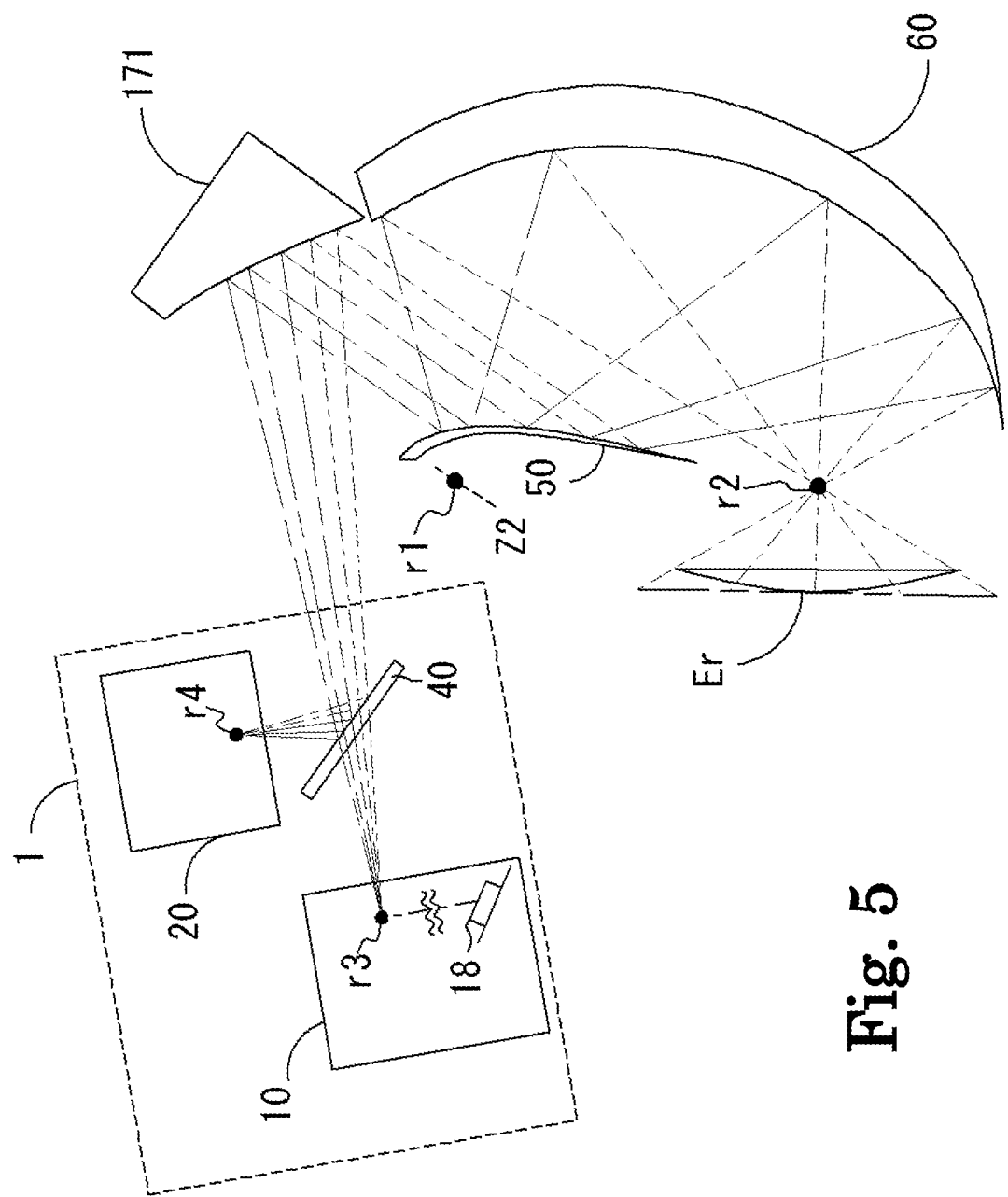
FIG. 5 is a view illustrating an objective optical system of a second example.

Hereinafter, a second example will be described with reference to FIG. 5. The same reference signs as those in the first example will be assigned to the same configuration elements of the second example as those in the first example, and description thereof will be omitted.

A difference between the second example and the first example is a portion of the scanning optical system 1 and the objective optical system 2. In the first example, the SLO optical system 10 and the OCT optical system 20 are telecentric with respect to an object side. In contrast, in the second example, light incident to the objective optical system 2 from the scanning optical system 1 (more specifically, the SLO optical system 10 and the OCT optical system 20) turns around a turning point at a finite distance from the objective optical system 2. In the second example, for descriptive purposes, light from the SLO optical system 10 is assumed to turn around the turning point r3 when incident to the objective optical system 2, and light from the OCT optical system 20 is assumed to turn around the turning point r4 when incident to the objective optical system 2.

The objective optical system 2 of the second example includes a paraboloidal mirror 171 between the first mirror 50 and the optical scanners 15 and 27 as the third mirror. The paraboloidal mirror 171 is a concave mirror which is disposed such that the focal point of the concave mirror coincides with the turning points r3 and r4. For this reason, light fluxes are telecentric on an object side of the paraboloidal mirror 171. In the second example, the paraboloidal mirror 171 is disposed such that the object axis (that is, the symmetrical axis of a paraboloidal surface) (not illustrated) of a mirror surface of the paraboloidal mirror 171 is parallel to the symmetrical axis z2 of the mirror surface of the first mirror 50. For this reason, similar to the first example, the first mirror 50 is irradiated with beams from the optical scanner 15 or 27 side (that is, the paraboloidal mirror 171) which are parallel to the symmetrical axis z2. As a result, light from the first mirror 50 toward the second mirror 60 turns around the first turning point r1 which is positioned where the focal point of the first mirror 50 overlaps with the focal point of the second mirror 60. Light is reflected by the second mirror 60, and thus, the light turns around the focal point r2 of the spheroidal mirror. Also, in the second example, as such, it is possible to decrease the swing angle of light incident to the objective optical system 2 (more specifically, the paraboloidal mirror 171) from the scanning optical system 1, and to satisfactorily scan a wide range on the fundus Er with light. As a result, it is possible to prevent partial deterioration of image quality of an image of the fundus which is caused by the incidence angle dependence of the optical path coupling member 40 (the dichroic mirror 40).

In a case where an image of the fundus is captured at a desired image angle, it is possible to decrease the swing angle of light in the optical scanners 15 and 27 by the extent of an increase in the focal distance of the paraboloidal mirror 171. For this reason, the paraboloidal mirror 171 having a longer focal distance within an allowable device size range is preferably adopted. As a result, it is considered that it is possible to more effectively reduce a problem of incidence angle dependence of the optical path coupling member 40.

The inventors of this application have confirmed that in a case where the optical system of the first example and the optical system of the second example are designed to conditions, better imaging performance is obtained in the second example than that in the first example.

The paraboloidal mirror 171 provided instead of the correction mirror systems 71 and 72 of the first example does not correct the inclination of an image plane. In contrast, in the second example, in order to prevent the inclination of an image plane in at least the SLO optical system 10, at least the detector 18 may be provided in such a way that the detector 18 is disposed inclined with respect to the optical axis of the light receiving optical system 10a. Furthermore, either the lens 12 or the lens 13 of the SLO optical system 10 may be disposed inclined with respect to the optical axis thereof. In the second example, the amount of inclination of the detector 18 is adjusted to have a Scheimpflug relationship with the fundus Er and the objective optical system 2. As a result, it is possible to prevent deterioration of image quality caused by the inclination of an image plane (that is, due to focus changing according to scan position).

Third Example

Hereinafter, a third example will be described with reference to FIG. 6. The same reference signs as those in the first example will be assigned to the same configuration elements of the third example as those in the first example, and description thereof will be omitted. A main difference between the third example and the first and second examples is the shape of the first mirror 50. In the third example, a mirror system is not provided between the first mirror 50 and the scanning optical system 1. In the third example, the scanning optical system 1 and the objective optical system 2 are partially different from those of the first example. In the first example, the SLO optical system 10 and the OCT optical system 20 are telecentric with respect to the object side. In contrast, in the third example, similar to the second example, light incident to the objective optical system 2 from the scanning optical system 1 (more specifically, the SLO optical system 10 and the OCT optical system 20) turns around a turning point at a finite distance from the objective optical system 2.

In the third example, the first mirror 50 is one hyperboloidal mirror (one of a pair of hyperboloidal surfaces). In the third example, a hyperboloidal mirror is an aspherical mirror that contribute to angle widening. Similar to the first example, the second mirror 60 may be a spheroidal mirror. The hyperboloidal mirror, that is, the first mirror 50 is disposed such that a virtual image side focal point (focal point on a convex surface side) coincides with the turning points r3 and r4. The first mirror 50 is disposed such that a real image side focal point (focal point on a concave surface side) coincides with one focal point of the second mirror 60. That is, the first mirror 50 is irradiated with light emitted from the virtual image side (hyperboloidal surface side which pairs with the first mirror 50) focal point. As a result, due to general characteristics of the hyperboloidal mirror, light reflected by the first mirror 50 turns around the rear image side focal point r1 of the first mirror 50 in correspondence with the driving of the optical scanner 15 (or the optical scanner 27). Since the focal point r1 is a focal point of the second mirror 60 which is a spheroidal mirror, the turning point of light reflected by the first mirror 50 is formed at the focal point r1 of the spheroidal mirror due to the disposition of the first mirror 50. In the third example, since light is reflected by the mirror surface of the first mirror 50, the swing angle of light from the first turning point r1 toward the second mirror 60 is further increased compared to the swing angle of light incident to the first mirror 50 from the scanning optical system 1. Light reflected by the second mirror 60 turns around a turning point, that is, the focal point r2 of the second mirror 60. Also, in the third example, as such, it is possible to decrease the swing angle of light incident to the objective optical system 2 (more specifically, the first mirror 50) from the scanning optical system 1, and to satisfactorily scan a wide range on the fundus Er with light.

The first mirror 50 of the third example is a hyperboloidal mirror (eccentricity >1). The mirror shape of the first mirror 50 becomes more similar to a paraboloidal shape illustrated in the first example as the eccentricity of a hyperboloidal surface approaches one. For this reason, as the eccentricity of the hyperboloidal surface approaches one, the virtual image side focal point (focal point on the convex surface side) becomes more distant from the mirror surface, and approaches infinity. For this reason, in a case where an image of the fundus is captured at a desired image angle, it is possible to further decrease the swing angle of light in the optical scanners 15 and 27 as the eccentricity of the first mirror 50 approaches one. For this reason, a hyperboloidal mirror having eccentricity closer to one within an allowable device size range is preferably adopted as the first mirror 50. As a result, it is considered that it is possible to more effectively reduce a problem of incidence angle dependence of the optical path coupling member 40.

Figure 6:
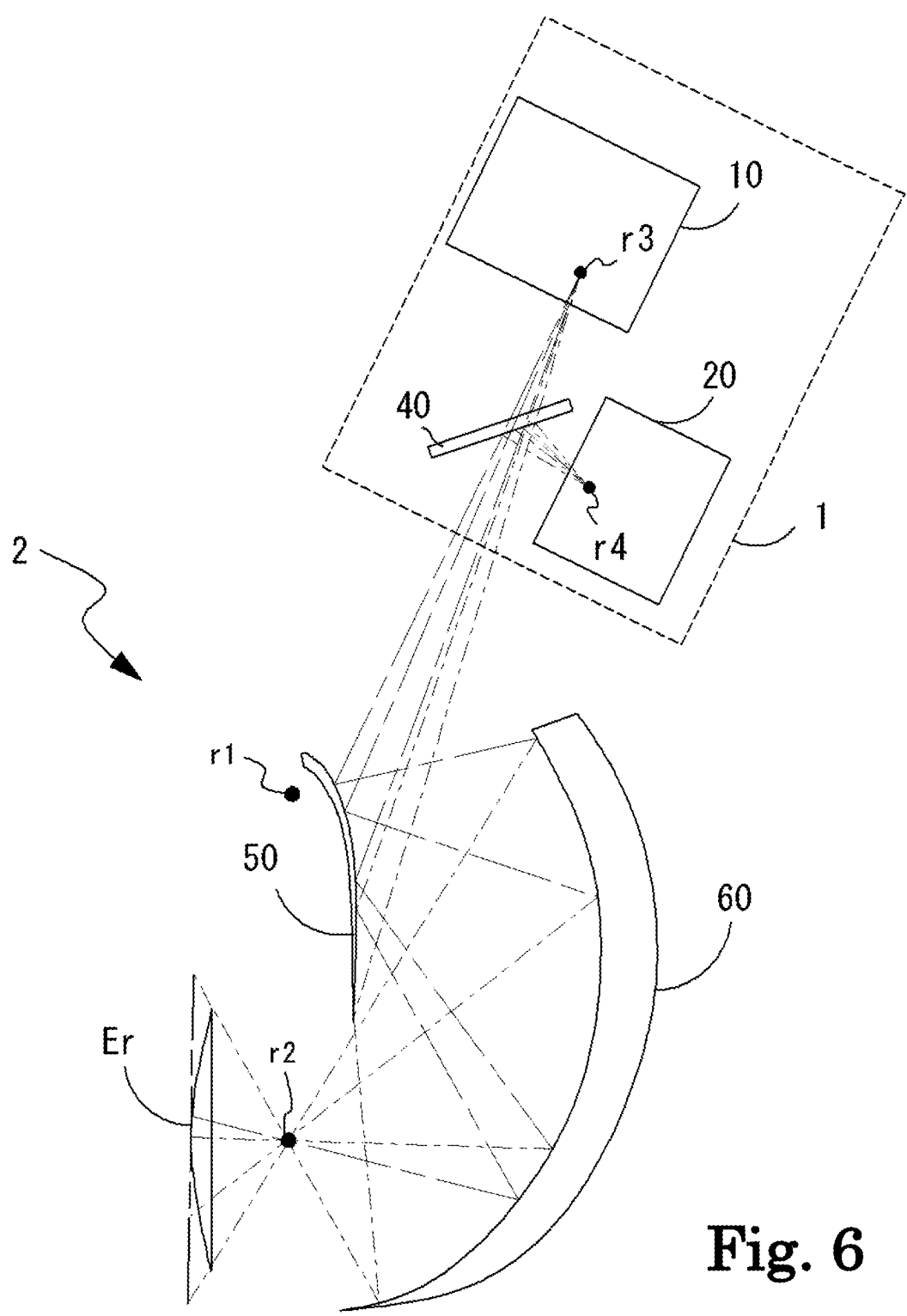
FIG. 6 is a view illustrating an objective optical system of a third example.

As illustrated in FIG. 6, the first mirror 50 may be disposed inclined with respect to the second mirror 60. In order to correct the inclination of an image plane occurring in this case, the detector 18 and the like of the SLO optical system 10 may be disposed inclined with respect to the optical axis.

Fourth Example

Figure 7:
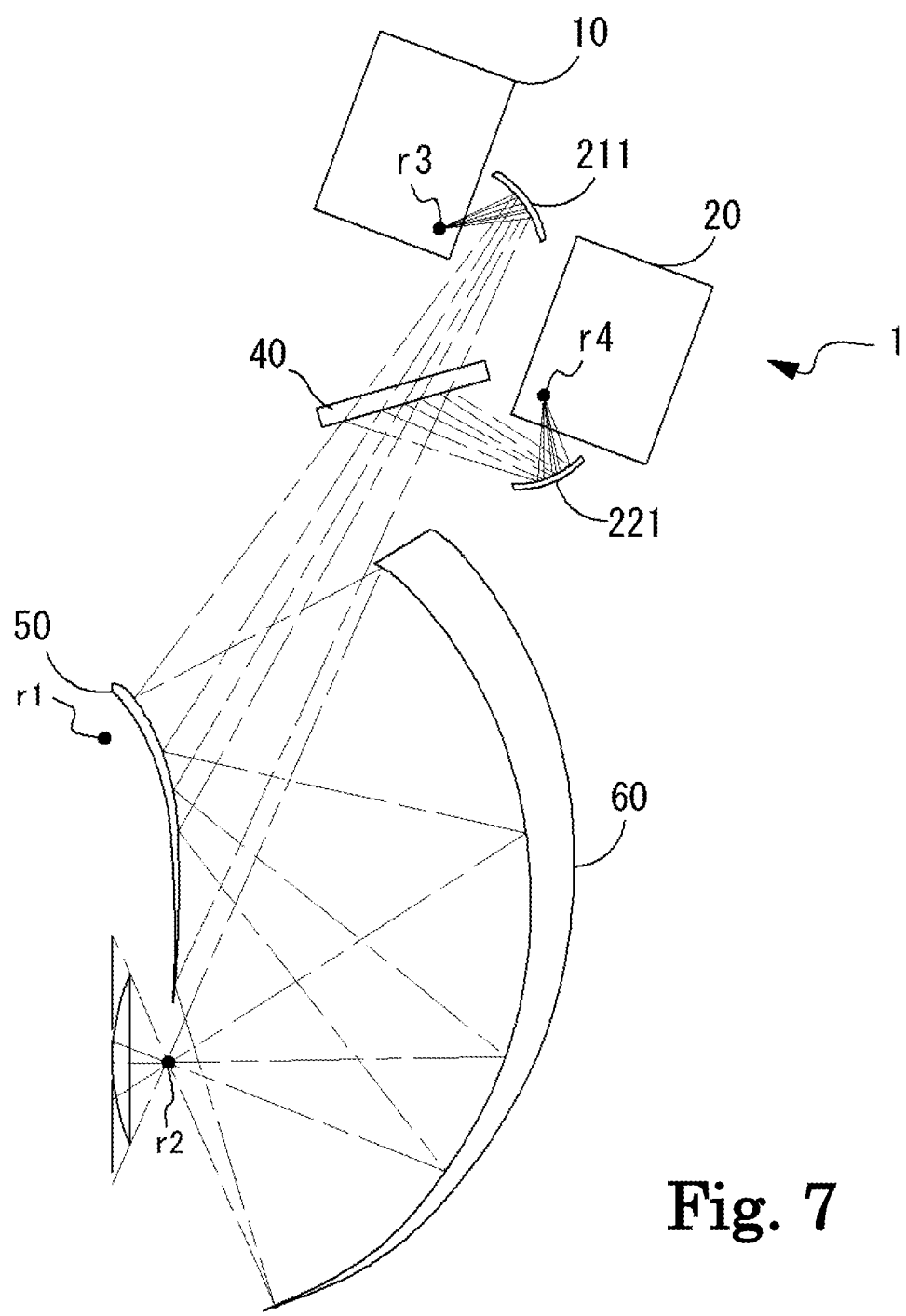
FIG. 7 is a view illustrating an optical system of a fourth example.

Hereinafter, a fourth example will be described with reference to FIGS. 7 and 8. A difference between the forth example and the third example is that the third mirrors 211 and 221 are further provided in the imaging device 100 in the fourth example. The third mirrors 211 and 222 are used to correct the eccentric aberration due to the objective optical 2. In FIG. 7, each of the SLO optical system 10 and the OCT optical system 20 is provided with one third mirror but not limited thereto. The SLO optical system 10 and the OCT optical 20 may share the common third mirror, similar to the first mirror 50 and the second mirror 60. The same reference signs as those in the third example will be assigned to the same configuration elements of the fourth example as those in the third example, and description thereof will be omitted.

Each of the third mirrors 211 and 221 is disposed between the first mirror 50 (hyperboloidal mirror) and the optical scanner 15, and between the first mirror 50 and the optical scanner 27, respectively. Accordingly, in FIG. 7, the light from the optical scanner 15 or 27 is reflected by the third mirror 211 or 221 once, and then incident to the first mirror 50.

In FIG. 7, the third mirrors 211 and 221 may be hyperboloidal mirrors. In this case, each of the first mirror 50 (hyperboloidal mirror), the second mirror 60 (ellipsoidal mirror) and the third mirrors 211 and 221 (hyperboloidal mirror) has a quadric surface, thus the optical system of the imaging device 100 can be configured at a relatively lower cost. Furthermore, in FIG. 7, the first mirror 50 has a convex surface as a reflective surface while the third mirrors 211 and 221 have concave surfaces as reflective surface.

The third mirrors 211 and 221 are disposed in such a way that focal points on the convex surface coincide with a focal point on the convex surface of the first mirror 50. Moreover, the focal point of the third mirror 211 and the optical scanner 15 are conjugate with respect to the third mirror 211. The focal point of the third mirror 221 and the optical scanner 127 are conjugate with respect to the third mirror 221. Consequently, the optical scanners 15 and 27 satisfactorily establish a conjugate relationship with the anterior ocular segment. The light turns around the focal points as turning points in correspondence with the operations of the optical scanners 15 and 27.

The third mirrors 211 and 221 can correct the inclination of an image plane which occurs due to the first mirror 50 and the second mirror 60 which are disposed eccentric.

<Example Applied to Odd-Order Aspherical Mirror or Free-Form Mirror as Third Mirror>

Hereinafter, a case in where one of the odd-order aspherical mirror or the free-form mirror, of which a base surface is paraboloidal surface, is employed as the third mirrors 211 and 221 of the fourth example.

FIG. 8 shows an enlarged view of the third mirror 211 which is the free-form mirror. In FIG. 8, a mirror surface of the third mirror 211 is represented by a solid line, and a hyperboloidal surface M which is a base surface of the third mirror 211 is represented by a dashed-dotted line.

The hyperboloidal surface M, which is the base surface, is disposed on the convex surface side of the first mirror 50. A focal point of the hyperboloidal surface M on the convex surface side coincides with the focal point of the first mirror 50 on the convex surface side. The optical scanners 15 and 27 are disposed at the other focal point of the hyperboloidal surface M (or at a conjugate position of the other focal point).

Furthermore, the third mirror 211 is formed in a mirror surface shape in such a way that a position of an imaginary object point (P2) coincides with that of the hyperboloidal surface M. The third mirror 211 is also formed in a mirror surface shape in such a way that a position of a surface apex (P1) coincides with that of the hyperboloidal surface M. That is, as illustrated in FIG. 8, the third mirror 211 and the hyperboloidal surface M have the imaginary object points and the surface apexes which coincide with each other, respectively, thus virtual images are slightly deviated (P3 and P4).

By employing such a mirror surface shape in the third mirror 211, a conjugate relationship of turning positions is easily maintained. At this time, it is desirable that the third mirror 211 has a mirror surface shape such that the virtual image (P4: virtual image by the actual mirror surface) is formed closer to the mirror surface than the virtual image (P3: virtual image by the hyperboloidal surface M). In particular, a shape of the free-form surface may be represented by the following expression:

$$\frac{cr^2}{1+\sqrt{1-(1+k)c^2r^2}} + \sum_{j=2} c_j x^m y^n$$

$$j = \frac{(m+n)^2 + m + 3n}{2} + 1$$

wherein z represents a sag quantity in parallel with z-axis (optical axis), c represents a curvature at the surface apex, k represents Conic constant, r represents a radius of curvature, and cj represents an integer of $x^m y^n$ term. Furthermore, in the example, by using the Conic constant and the radius of curvature which have values the same (having the same first term) as those of the quadric surface (the hyperboloidal surface in this case) which is the base surface, it is possible to simultaneously achieve pupil imaging relationship and reduction in aberration.

The third mirror 212 has a mirror surface shape which can be represented by the same expression as that of the third mirror 211.

The exemplified case where the free-form mirror is applied as the third mirrors 211 and 221 has been described. In a case where the odd-order polynomial aspherical mirror is employed as the third mirrors 211 and 221, it is also desirable that the third mirrors 211 and 221 have a mirror surface shape in which positions of an imaginary object point and a surface apex coincide with those of a hyperboloidal surface which is a base surface. In this case, the mirror surface shape may be represented by, for example, the following expression:

$$z = \frac{cr^2}{1+\sqrt{1-(1+k)c^2r^2}} + AR1r + AR2r^2 + \ldots + ARnr^n + \ldots AR30r^{30}$$

wherein z represents a sag quantity in parallel with z-axis (optical axis), c represents a curvature at the surface apex, k represents Conic constant, r represents a radius of curvature, and ARn represents a coefficient. The Conic constant and the radius of curvature may have values the same (having the same first term) as those of the hyperboloidal surface which is the base surface, similar to the case where the free-form mirror is used as the third mirror.

An optical element may be provided between the third mirrors 211 and 221, and a detector receiving fundus reflected light (for example, the detector 18) to correct the eccentric aberration. For example, in FIG. 8, the condenser lens 17 (not shown) is eccentrically disposed in one direction with respect to the optical axis of the light receiving optical system 10a so as to correct the rotational symmetrical eccentric aberration. However, the optical element correcting the eccentric aberration is not limited to the eccentrically disposed condenser lens 17.

Fifth Example

Hereinafter, a fifth example will be described with reference to FIG. 9. FIG. 9 shows an optical system which is provided between the examinee's eye E and the intermediate image. The fifth example further includes an optical system 300 (referred to as a "second correction mirror system") correcting the eccentric aberration between the paraboloidal mirror 171 and the detector (the detector 18) receiving the fundus reflected light, of the second example. That is, the fifth example includes the objective optical system 2 having the first mirror 50 (paraboloidal mirror), the second mirror 60 (ellipsoidal mirror) and the third mirror (the paraboloidal mirror 171), each of which has a mirror surface shape that is a quadric surface.

The optical system of the fifth example is able to satisfactorily suppress an influence of the eccentric aberration in a case where the objective optical system 2 is downsized. In other words, it is required to increase refractive power of each reflective surface in the objective optical system 2 upon downsizing. However, the generated amount of the eccentric aberration increases as the refractive power of the reflective surface increases. The second correction mirror system 300 including the free-form mirror corrects the eccentric aberration which occurs due to downsizing. Furthermore, the second correction mirror system 300 may include the odd-order aspherical mirror instead of the free-form mirror, and may correct the eccentric aberration by the odd-order aspherical mirror.

In the fifth example, the second correction mirror system 300 also corrects the inclination of an image plane which occurs due to the eccentric arrangement between the first mirror 50 (paraboloidal mirror) and the second mirror 60. That is, the second correction mirror system 300 also functions as the "correction mirror system."

The second correction mirror 300 of the embodiment includes, as an example, three mirrors 301, 302 and 303. The concave mirror 301, the convex mirror 302 and the concave mirror 303 are arranged from the paraboloidal surface 171 side toward the detector 18 in this order. At least one of the mirrors included in the second correction mirror system 300 may be the free-form mirror. At this time, a mirror having the strongest power, out of the mirrors included in the second correction mirror system 300, may be the free-form mirror. For example, in FIG. 9, the mirrors 301 and 302 may be the spherical mirrors while a concave mirror 303 disposed right before the intermediate image Ic1 may be the free-form mirror. The lesser a number of the free-form mirrors in the mirrors included in the second correction mirror system 300, the more advantages the optical system can obtain in terms of cost and accuracy. However, it is not limited to such a configuration, two or more mirrors, out of the mirrors included in the second correction mirror system 300, may be the free-form mirrors. It is the same for a case where the odd-order aspherical mirror is used instead of or with the free-form mirror.

Furthermore, a shape and arrangement of each free-form mirror may be appropriately designed by means of optical simulation or the like.

<Operation of Device when Acquiring Tomographic Image>

The objective optical system 2 of the examples is an objective mirror system that forms a turning point (the turning point r2 in the examples), which turns in correspondence with the operation of the optical scanner 27, in the anterior ocular segment (for example, the position of the pupil) of the examinee's eye E via mirror systems (the first mirror 50, the second mirror 60, and the like) which are disposed between the examinee's eye E and the optical scanner 27. In the objective optical system 2 of the examples, the second mirror 60 immediately before the examinee's eye E is a spheroidal mirror, and the turning point r2 is formed at one of the two focal points r1 and r2 of the spheroidal mirror. The optical path length of light, which is incident to the mirror surface from one of the two focal points of the spheroidal mirror and is guided to the other focal point, is always the same between the two focal points. In contrast, in the examples, mirrors such as the first mirror 50 are disposed between the optical scanner 27 and the second mirror 60, and thus, the distance of measurement light from the optical scanner 27 to the second turning point r2 differs according to scan position of the optical scanner 27.

In the examples, the optical path length of measurement light from the second turning point (position of the pupil) r2 to a front surface of the fundus Er also differs between scan positions. That is, due to curvature of the fundus, the distance of measurement light from the second turning point r2 to the fundus Er differs according to scan position of the optical scanner 27.

It is considered that the distance of measurement light from the optical scanner 27 to the examinee's eye E differs between scan positions of the optical scanner 27. That is, it is considered that a change in an optical path length difference between measurement light and reference light occurs due to the distance of measurement light from the optical scanner 27 to the examinee's eye E at each scan position of the optical scanner 27.

It is considered that in a case where depth profiles (OCT data) are obtained in this state based on signal from the detector 31, a depth position in an area, in which the depth profiles (OCT data) of the examinee's eye E are obtained, differs between scan positions of the optical scanner 27. It is considered that since an optical path length difference depending on scan position, a deviation between a range in which the sensitivity of the detector 31 is high and a range in which interference between measurement light and reference light occurs is relatively large.

In contrast, the control unit 70 corrects a change in an optical path length difference between measurement light and reference light caused by the distance of measurement light from the optical scanner 27 to the examinee's eye E at each scan position of the optical scanner 27.

A change in an optical path length difference between measurement light and reference light may be corrected via processing of data (via processing of OCT data). The control unit 30 may correct information regarding position in the depth direction for OCT data when the control unit 30 acquires the OCT data based on signals from the detector 31.

When forming two-dimensional OCT data by aligning multiple items of OCT data, the control unit 30 may correct a relative depth position between the OCT data for scan positions.

It is possible to obtain good OCT data (or two-dimensional OCT data) as the result of performing such a process.

A change in an optical path length difference between reference light and measurement light may be optically corrected. For example, correction may be performed by controlling the driving of the optical path length adjustment mechanism (drive mechanism) 25a in correspondence with the scan position of the optical scanner 27. As described above, the drive mechanism 25a may adjust an optical path length difference between measurement light and reference light by displacing an optical member (for example, a mirror) disposed on optical paths of the reference light (or optical paths of the measurement light). For example, in the examples, the drive mechanism 25a changes the optical path length of reference light in correspondence with a change in the optical path length of measurement light caused by the operation of the optical scanner 27. As a result, signals based on interference between measurement light and reference light are likely to be detected in a range in which the sensitivity of the detector 31 is high, and it is possible to obtain good OCT data (or two-dimensional OCT data). In this case, preferably, it is possible to decrease the range of change in an optical path length difference such that, regardless of scan position, signals based on interference between measurement light and reference light are detected in a range in which the sensitivity of the detector 31 is relatively high. The driving of the drive mechanism 25a is not necessarily required to be controlled such that an optical path length difference between measurement light and reference light is the same (for example, zero) between scan positions.

The control unit 70 corrects a change in an optical path length difference between measurement light and reference light while taking into consideration at least a change in the distance (optical path length) of the measurement light from the optical scanner 27 to the second turning point r2. The control unit 70 may perform correction while taking into consideration a change in the optical path length of measurement light between scan positions (that is, a change in the optical path length of measurement light from the second turning point r2 to the fundus Er) caused by the curvature of the fundus. A relationship between the optical path length of measurement light from the optical scanner 27 to the second turning point r2 and scan positions of the optical scanner 27 is determined by design of an optical system. A relationship between the optical path length of measurement light from the second turning point to the fundus Er and scan positions of the optical scanner 27 is also determined by design (mainly swing angle with respect to the second turning point) of an optical system.

For example, a correction table, in which the amounts of correction (for example, the amounts of change of an optical path length, or the amounts of correction of information regarding position in the depth direction for OCT data) required to correct changes in an optical path length difference are mapped to scan positions of the optical scanner 27, may be prepared in the memory 72 in advance. The control unit 70 may correct a change in an optical path length difference using the correction table. The amounts of correction in the table are values determined in consideration of at least a change in the optical path length of measurement light from the optical scanner 27 to the second turning point r2. The amounts of correction may be values determined in consideration of a change in an optical path length from the second turning point r2 to the fundus Er. A relationship between an optical path length difference and the amount of correction (in other words, a relationship between scan position and the amount of correction) may be obtained in advance via simulation, calibration, and the like.

In the examples, the optical scanner 27 includes two optical scanners. That is, the optical scanner 27 includes a first optical scanner (for example, an X galvanometer scanner) that performs a horizontal scan of a target with measurement light, and a second scanner (for example, a Y galvanometer scanner) that performs a vertical scan of the target with measurement light in a direction intersecting a horizontal scan direction. In a case where the horizontal scan is performed in a depth direction of each drawing sheet, and the vertical scan is performed in a direction intersecting the depth direction of the drawing sheet, it is possible to adopt the objective optical system 2 that causes a change in the optical path length of measurement light (more specifically, a change in an optical path length from the optical scanner 27 to the second turning point r2) in correspondence with only the positions of vertical scan. For example, as in the embodiment, it is possible to realize the objective optical system 2 by using a concave mirror and a convex mirror which have rotating curved surfaces of a spheroidal mirror and a rotating paraboloidal mirror.

The control unit 30 may acquire two-dimensional OCT data for multiple scan lines by perform a raster scan of the objective optical system 2 with measurement light. That is, the control unit 30 acquires multiple items of two-dimensional OCT data, which is acquired due to performing a horizontal scan, for different scan lines in a vertical scan direction by controlling the driving of the optical scanner 27. The driving of the drive mechanism 25a may be controlled in correspondence with the scan position of the second scanner. That is, a change in an optical path length difference between reference light and measurement light may be corrected by driving the drive mechanism 2 in correspondence with the scan position of the second scanner.

In this case, a change in an optical path length difference between measurement light and reference light may occur due to vertical scan, and in contrast, the speed of vertical scan is slower than that of horizontal scan. For this reason, it is possible to prevent a change in an optical path length difference over time. Accordingly, it is possible to drive the drive mechanism 25a such that a change in an optical path length difference between reference light and measurement light is more reliably corrected. As a result, it is possible to acquire multiple items of good two-dimensional OCT data.

The description has been given based on the embodiment; however, this disclosure is not limited to the embodiment, and change may be made in various forms.

In the first to fifth examples, the second mirror 60 of the objective optical system 2 is a spheroidal mirror, and the first mirror 50 used in combination therewith is a paraboloidal mirror or a hyperboloidal mirror. In other words, in the first to fifth examples, the first mirror 50 has a curve surface formed along a trajectory that is obtained by rotating a quadratic curve having eccentricity ≤1 around a symmetrical axis. As described above, the curved surface shape of each of the first mirror 50 and the second mirror 60 may be suitably selected from various quadric surfaces, various aspherical surfaces, or various free-form surfaces. Furthermore, in a case where the first mirror 50 and the second mirror 60 are formed to have an odd-order aspherical surface or a free-form surface, mirror surface shapes may be represented by using the expression shown in the third example. That is, it is possible to employ a mirror surface shape which can be represented, with any one of quadric surfaces considered as a base surface, using Conic constant and a radius of curvature of the quadric surface in the first mirror 50 and the second mirror 60.

Moreover, in the scanning optical system 1 of the embodiment, two imaging optical systems (the SLO optical system 10 and the OCT optical system 20 in the embodiment) respectively include optical scanners, and respective optical paths of the two imaging optical systems are coupled together by the optical path coupling member 40. This disclosure is not necessarily limited to that configuration. Alternatively, in the scanning optical system 1, optical paths of an imaging optical system and optical paths of an irradiation optical system which emits therapy light or stimulating light may be coupled together by the optical path coupling member 40. The imaging optical system referred to here may scan the fundus with light from a first light source for capturing an image by driving a first optical scanner, and may include a detector that receives fundus reflected light of light from the first light source. In this case, either the SLO optical system 10 or the OCT optical system 20 of the embodiment may be used as the imaging optical system. In contrast, light with which the examinee's eye E is irradiated with the irradiation optical system may be therapy laser beams which coagulate the fundus with light. The light may be stimulating light for visual field test. Needless to say, the therapy light or the stimulating light are not limited to those purposes. The irradiation optical system may include at least a second optical scanner that determines the irradiation position of light on the fundus by deflecting light from a second light source emitting therapy light or stimulating light. The irradiation optical system may be replaced with either the SLO optical system 10 or the OCT optical system 20 of the embodiment. The second optical scanner may be replaced with either the optical scanner 15 or the optical scanner 27 of the embodiment, and the replacement one may be disposed.

The optical system shown in the fifth example, especially, may be employed in a projector system for wearable devices such as a head-mounted device. As one example, the optical system may be used as a retina scanning display. As described in Reference 1 (described below), such optical system can serve as an optical system for the retina scanning display by performing laser scanning in the SLO optical system in correspondence with a video signal. In recent years, the retina scanning display has been proposed to be used in a perimeter. However, the conventional technologies described in Reference 2 have a problem that a scannable angle is small, and do not suggest or teach an idea of extending a scan angle. By employing the optical system of the fifth example, it is possible to perform the visual field test of ultrawide visual field with a head-mounted device.

In this case, a wearable perimeter may be used. For example, a stimulus visual target may be projected from a display element to a retina by arranging the display element (e.g. LCD) on a fundus conjugate surface which is disposed opposing to the examinee's eye E sandwiching the second correction mirror system 300 of FIG. 9 therebetween.

REFERENCES

Reference 1: Flying Spot TV Ophthalmoscope Applied Optics 19(17) 2991-2997, 1980
Reference 2: JP-A-H10-272098

<OCT Imaging of Anterior Ocular Segment>

The fundus imaging device 1 of the embodiment can acquire fundus OCT data (for example, a tomographic image, OCT angiography or the like). The fundus imaging device 1 may further acquire anterior ocular segment (also referred to as "AOS") OCT data. At this time, the fundus imaging device 1 may switch imaging modes including a fundus imaging mode for acquiring fundus OCT data and an AOS imaging mode for acquiring AOS OCT data. Before and after switching the imaging modes, the control unit 70 changes, for example, at least one of diopter of the OCT optical system 20 and an optical path length difference between a measurement light path and a reference light path.

Moreover, in a case where the AOS OCT data is acquired, the turning point r2 (see FIGS. 5, 6, 7 and 9) formed by the objective optical system 2 is preferably formed at a curvature center of the cornea. In this case, the measurement light is easily incident perpendicularly to a corneal surface, thus an orientation of the measurement light is hardly changed due to the cornea. Moreover, by employing the objective optical system with a wide image angle of the embodiment, the OCT data can be easily acquired in a wide region between angles. As a result, the satisfactory OCT data can be easily acquired for the cornea.

Moreover, in a case where the AOS OCT data is acquired, a diopter correction unit (not shown) of the OCT optical system 20 may be adjusted such that the measurement light is focused on the AOS. At this time, a focusing position of the measurement light may be appropriately set, for example, in a range from a corneal surface to a rear surface of crystalline lens. The diopter correction unit may be a well-known focus adjustment mechanism which is provided on the measurement light path of the OCT optical system 20.

Furthermore, in a case where the AOS OCT data is acquired, the optical path length difference between the measurement light path and the reference light path may be adjusted such that a zero-delay position where the optical path length difference between the measurement light path and the reference light path is 0 is in the vicinity of the AOS.

In a case where the fundus imaging mode is switched to the AOS imaging mode, the control unit 70 may perform at least one of the aforementioned adjustment operations. As a result of the adjustment operations, acquiring the AOS OCT data is smoothly initiated.

<Example Applied to Fundus Camera>

This disclosure may be employed in, for example, a fundus camera instead of the fundus imaging device with the optical scanner. In this case, a fundus camera optical system may be provided instead of at least one of the SLO optical system 10 and the OCT optical system 20. The fundus camera optical system may further include a projective optical system and an imaging optical system. At this time, the projective optical system and the imaging optical system may share the same objective optical system.

The projective optical system irradiates the fundus with light (illumination light) via the objective optical system 2. A light source and an aperture may be disposed such that an apparent light source position in the projective optical system is disposed at positions of the optical scanner 15 and 27 of the embodiment. The imaging optical system may include an imaging element (two-dimensional light receiving element) at a fundus conjugate position.

In this case, the apparent light source position is relayed to the position of each of the turning points r1 and r2 of the example, and the light from the light source is irradiated at the fundus. The fundus reflected light forms an image on the imaging element, and a fundus image is taken.

Each of the first mirror 50 and the second mirror 60 reflects the illumination light from the light source to relay the light from apparent light source to the AOS. The third mirror may be provided between the first mirror 50 and the fundus camera optical system to reduce the eccentric aberration which occurs due to the first mirror 50 and the second mirror 60.

The fundus camera can be represented as below: a fundus camera including an objective optical system formed of a plurality of eccentrically disposed mirrors; and a fundus camera optical system which has a projective optical system that irradiates a fundus with illumination light from a light source via the objective optical system and an imaging optical system that takes a fundus image based on fundus reflected light, and further including a correction mirror for correcting an eccentric aberration which occurs due to eccentric arrangement of the plurality of mirrors, which is disposed in the objective optical system or between the objective optical system and the fundus camera optical system. The correction mirror may be any one of the first to third mirrors state above.

<Properties of Line-Scanning SLO>

In this disclosure, the following fundus imaging devices (A1) to (A4) and (B1) to (B5) are disclosed as means for solving various problems which may occur when a wide-range image is captured using a line-scanning SLO.

A fundus imaging device (A1) includes: a line-scanning SLO optical system that includes an optical scanner which scans line-shaped light guided from a light source, and a line sensor or an area sensor which receive fundus reflected light; and an objective optical system that is disposed between the optical scanner and an examinee's eye, and includes a curved mirror which is disposed at a focal point of the examinee's eye, and a distortion correction optical system which guides light from the optical scanner to the curved mirror and cancels out distortion of an image plane caused by the curved mirror.

In the fundus imaging device (A1), distortion of an image plane which occurs due to the second mirror 60 (an example of a "curved mirror") is cancelled out (in other words, is reduced) by mirrors (a combination of the first mirror 50 and the correction mirror systems 71 and 72, or a combination of the first mirror 50 and the correction mirror 171) disposed between the second mirror 60 and the optical scanners 15 and 27. The distortion correction optical system is not necessarily formed of only reflective elements such as mirrors. For example, the distortion correction optical system may include refractive elements such as lenses partially or in its entirety. A refractive element may reduce distortion of an image plane which occurs due to a "curved mirror". Specifically, a refractive element may be a lens that is disposed eccentric with respect to the optical axis thereof, may be an aspherical lens, or may be other configuration elements.

In a fundus imaging device (A2) with a configuration as set forth in the fundus imaging device (A1), the curved mirror is an ellipsoidal mirror which has a first focal point and a second focal point, and the optical scanner and the examinee's eye are respectively disposed at a conjugate position of the first focal point and the second focal point, and the distortion correction optical system is disposed between the optical scanner and the first focal point or between the first focal point and the second focal point.

In the fundus imaging device (A2), in a case where the distortion correction optical system is disposed between the optical scanner and the first focal point, the optical scanner may be disposed at the first focal point.

In a fundus imaging device (A3) with a configuration as set forth in the fundus imaging device (A1), a line sensor or an area sensor is disposed inclined to have a Scheimpflug relationship with a fundus and the objective optical system, or the fundus imaging device further includes an optical member that correct the inclination of an image plane which occurs as the fundus reflected light passes through the objective optical system.

In a fundus imaging device (A4) with a configuration as set forth in the fundus imaging device (A3), the optical member is disposed on light receiving optical paths of fundus reflected light between the optical scanner and the line sensor or the area sensor in the line-scanning SLO optical system, and are independent from projected light optical paths of light from the light source.

A fundus imaging device (B1) includes:
a line-scanning SLO optical system that includes an optical scanner which scans line-shaped light guided from a light source, and a line sensor or an area sensor which receives fundus reflected light; and
an objective optical system that is disposed between the optical scanner and an examinee's eye, includes at least one curved mirror, and guides light through a turning point of the light formed at a focal point of the curved mirror by reflecting the light from the light source which is guided from the optical scanner,
in which the line sensor or the area sensor is disposed inclined to have a Scheimpflug relationship with a fundus and the objective optical system, or
the fundus imaging device further includes an optical member that corrects an inclination of an image plane which occurs as the fundus reflected light is reflected by the curved mirror.

In a fundus imaging device (B2) with a configuration as set forth in the fundus imaging device (B1), the curved mirror is an ellipsoidal mirror which has a first focal point and a second focal point, and the optical scanner is disposed at a conjugate position of the first focal point and the examinee's eye is disposed at the second focal point.

In a fundus imaging device (B3) with a configuration as set forth in the fundus imaging device (B2), the objective optical system further includes a distortion correction optical system that guides light from the optical scanner to the curved mirror and cancels out distortion of an image plane caused by the curved mirror.

In a fundus imaging device (B4) with a configuration as set forth in the fundus imaging device (B3), the distortion correction optical system is disposed between the optical scanner and the first focal point, or between the first focal point and the second focal point.

In a fundus imaging device (B5) with a configuration as set forth in the fundus imaging device (B1), the optical member is disposed on light receiving optical paths of fundus reflected light between the optical scanner and the line sensor or the area sensor in the line-scanning SLO optical system, and are independent from projected light optical paths of light from the light source.

<Other Embodiments>

In this disclosure, the following fundus imaging devices (C1) to (C21) and (D1) to (D2) are further disclosed.

A fundus imaging device (C1) includes:
a scanning optical system that includes an optical scanner which changes a travelling direction of light from a light source to scan a fundus of an examinee's eye with the light; and
an objective optical system that is disposed between the optical scanner and the examinee's eye, and guides the light from the optical scanner to the fundus,
in which the fundus imaging device forms an image of the fundus based on light being the light returned from the fundus, the objective optical system is an eccentric optical system disposed between the optical scanner and the examinee's eye and having at least a first mirror and a second mirror, each optical surface of the first mirror and the second mirror is eccentric, the first mirror reflects the light from the optical scanner and forms a first turning point around which the light turns in correspondence with an operation of the optical scanner, the second mirror further reflects the light reflected by the first mirror and forms a second turning point around which the light emitted to the examinee's eye turns, and the fundus imaging device further includes a third mirror which is disposed between the optical scanner and the first mirror to correct an eccentric aberration in the objective optical system.

In a fundus imaging device (C2) with a configuration as set forth in the fundus imaging device (C1), each of the first mirror and the third mirror is one of a hyperboloidal mirror, a free-form mirror of which a base surface is a hyperboloidal surface, and an odd-order aspherical mirror of which a base surface is a hyperboloidal surface.

A fundus imaging device (C3) with a configuration as set forth in the fundus imaging device (C2) further includes a light receiving optical system which receives the fundus reflected light via at least the objective optical system and the optical scanner, and a first optical member which is disposed between the light receiving element and the optical scanner to correct an eccentric aberration.

In a fundus imaging device (C4) with a configuration as set forth in the fundus imaging device (C3), the first optical member is an eccentric lens which is eccentrically disposed with respect to an optical axis of the light receiving optical system.

In a fundus imaging device (C5) with a configuration as set forth in the fundus imaging device (C3), the first optical member is a quadric mirror.

In the fundus imaging device (C5) with a configuration as set forth in the fundus imaging device (C3), the first optical member is a free-form mirror or an odd-order aspherical mirror.

In a fundus imaging device (C6) with a configuration as set forth in the fundus imaging device (C1), each of the first mirror and the third mirror is one of a paraboloidal mirror, a free-form mirror of which a base surface is a paraboloidal surface, and an odd-order aspherical mirror of which a base surface is a paraboloidal surface.

In a fundus imaging device (C7) with a configuration as set forth in the fundus imaging device (C1), each of the first mirror and the third mirror is a free-form mirror of which a base surface is a spherical surface or a plane surface.

In the fundus imaging device (C7) with a configuration as set forth in the fundus imaging device (C2), (C6) or (C7), the third mirror has smaller power compared with the first mirror and the second mirror.

In a fundus imaging device (C8) with a configuration as set forth in the fundus imaging devices (C2), (C6) or (C7), the free-form surface or the odd-order aspherical surface has a base surface which is a quadric surface satisfying a conjugate relationship between the optical scanner and an anterior ocular segment of the examinee's eye.

In a fundus imaging device (C9) with a configuration as set forth in the fundus imaging device (C8), at least one of focal points of a quadric surface being the base surface of the free-form surface or the odd-order aspherical surface coincides with the first turning point.

A fundus imaging device (C10) with a configuration as set forth in the fundus imaging device (C1) further includes an optical member which corrects an inclination of an image plane which occurs as the fundus reflected light is reflected by each mirror of the objective optical system.

A fundus imaging device (C11) with a configuration as set forth in the fundus imaging device (C10) further include a correction mirror system that corrects the inclination of the image plane, as the optical member, in which the correction mirror system is disposed between the optical scanner and a third mirror disposed between the optical scanner and the first mirror, and the third mirror corrects an eccentric aberration in the objective optical system.

In a fundus imaging device (C12) with a configuration as set forth in the fundus imaging device (C10), the scanning optical system includes a line sensor or an area sensor as a detector receiving the fundus reflected light, and a line-scanning SLO optical system which scans the fundus with line-shaped light fluxes using the optical scanner, the optical member is the detector disposed inclined with respect to an optical axis.

In a fundus imaging device (C13) with a configuration as set forth in the fundus imaging device (C12), the detector is disposed inclined to have a Scheimpflug relationship with the fundus and the objective optical system.

In a fundus imaging device (C14) with a configuration as set forth in the fundus imaging device (C1), a swing angle of light incident to the first mirror is smaller than a swing angle of the light at the second turning point, in the objective optical system.

In a fundus imaging device (C15) with a configuration as set forth in the fundus imaging device (C1), the first mirror turns the light incident to the second mirror from the first turning point around the first turning point at a larger swing angle than a swing angle of the light incident to the first mirror from the third mirror.

In a fundus imaging device (C16) with a configuration as set forth in the fundus imaging device (C15), the first mirror forms the first turning point at a focal point of the first mirror, and the second mirror has two focal points, and is configured that the first turning point is positioned at one focal point of the second mirror to form the second turning point at the other focal point of the second mirror.

In a fundus imaging device (C17) with a configuration as set forth in the fundus imaging device (C15), the third mirror has two focal points, and disposes a fourth turning point around which light that is incident to the objective optical system from the scanning optical system turns at one focal point, so as to form a third turning point around which light that is incident to the objective optical system from the scanning optical system turns at the other focal point; the first mirror has two focal points, and disposes the third turning point at one focal point so as to form the first turning point at the other focal point; and the second mirror has two focal points, and disposes the first turning point at one focal point so as to form the second turning point at the other focal point.

In a fundus imaging device (C18) with a configuration as set forth in the fundus imaging device (C1), the first mirror corrects asymmetric distortion of an image plane which occurs due to the second mirror.

In a fundus imaging device (C19) with a configuration as set forth in the fundus imaging device (C1), the first mirror has the strongest power in the objective optical system.

In a fundus imaging device (C20) with a configuration as set forth in the fundus imaging device (C1), the scanning optical system includes:
an SLO optical system that includes a first optical scanner which scans light from a first light source, and obtains a front image of the fundus using light from the first light source,
an OCT optical system that includes a second optical scanner which scans measurement light from a second light source, and obtains a tomographic image of the examinee's eye using optical interferometry, and
an optical path coupling member that couples an optical path of the SLO optical system and an optical path of the OCT optical system between the first optical scanner and the first mirror and between the second optical scanner and the first mirror.

In a fundus imaging device (C21) with a configuration as set forth in the fundus imaging device (C20), the SLO optical system and the OCT optical system are telecentric on an object side.

A fundus imaging device (D1) includes an objective optical system formed of a plurality of eccentrically disposed mirrors, a projective and photoreceptive optical system including a projective optical system that irradiates a fundus with light from a light source using the objective optical system and a photoreceptive optical system that receives the fundus reflected light, and a correction mirror that corrects an eccentric aberration which occurs due to eccentric arrangement of the plurality of mirrors, in which the correction mirror is disposed in the objective optical system or between the objective optical system and the projective and photoreceptive optical system.

In a fundus imaging device (D2) with a configuration as set forth in the fundus imaging device (D1), the projective optical system irradiates the fundus with illumination light, and the imaging optical system is provided with an imaging element which takes a fundus image based on fundus reflected light of the illumination light.

What is claimed is:

1. A fundus imaging device comprising:
a scanning optical system that includes an optical scanner configured to change a travelling direction of light from a light source to scan a fundus of an examinee's eye with the light; and
an objective optical system that is disposed between the optical scanner and the examinee's eye, and is configured to guide the light from the optical scanner to the fundus,
wherein the fundus imaging device forms an image of the fundus based on fundus reflected light being the light reflected from the fundus,
the objective optical system includes:
a first mirror configured to reflect the light from the optical scanner, and to form a first turning point around which the light turns in correspondence with an operation of the optical scanner; and
a second mirror configured to further reflect the light reflected by the first mirror, and to form a second turning point around which the light emitted to the examinee's eye turns, and
at least one of the first mirror and the second mirror has a mirror surface being a free-form surface or an odd-order aspherical surface.

2. The fundus imaging device according to claim 1, wherein at least one of the first mirror and the second mirror has a mirror surface being an odd-order aspherical surface mirror.

3. The fundus imaging device according to claim 1, wherein a swing angle of light incident to the first mirror is smaller than a swing angle of the light at the second turning point.

4. The fundus imaging device according to claim 1, wherein one of which power is smaller, out of the first mirror and the second mirror, has a mirror surface being the free-form surface or the odd-order aspherical surface.

5. The fundus imaging device according to claim 1, further comprising:
a third mirror that is disposed between the optical scanner and the first mirror, and is configured to correct an eccentric aberration in the objective optical system.

6. The fundus imaging device according to claim 5, wherein the third mirror has smaller power compared with the first mirror and the second mirror.

7. The fundus imaging device according to claim 5, wherein the first mirror turns the light incident to the second mirror from the first turning point around the first turning point at a larger swing angle than a swing angle of the light incident to the first mirror from the third mirror.

8. The fundus imaging device according to claim 7, wherein the first mirror forms the first turning point at a focal point of the first mirror, and
the second mirror has two focal points, and is configured that the first turning point is positioned at one focal point of the second mirror to form the second turning point at the other focal point of the second mirror.

9. The fundus imaging device according to claim 1, wherein the free-form surface or the odd-order aspherical surface has a base surface which is a quadric surface satisfying a conjugate relationship between the optical scanner and an anterior ocular segment of the examinee's eye.

10. The fundus imaging device according to claim 9, wherein at least one of focal points of the quadric surface being the base surface of the free-form surface or the odd-order aspherical surface coincides with the first turning point.

11. The fundus imaging device according to claim 1, further comprising:
an optical member configured to correct an inclination of an image plane which occurs as the fundus reflected light is reflected by each mirror of the objective optical system.

12. The fundus imaging device according to claim 11, further comprising:
a correction mirror system configured to correct the inclination of the image plane, as the optical member,
wherein the correction mirror system is disposed between the optical scanner and a third mirror disposed between the optical scanner and the first mirror, and
the third mirror is configured to correct an eccentric aberration in the objective optical system.

13. The fundus imaging device according to claim 11, wherein the scanning optical system comprises a line sensor or an area sensor as a detector configured to receive the fundus reflected light, and a line-scanning SLO optical system configured to scan the fundus with line-shaped light fluxes using the optical scanner, and
the optical member is the detector disposed inclined with respect to an optical axis.

14. The fundus imaging device according to claim 13,
wherein the detector is disposed inclined to have a Scheimpflug relationship with the fundus and the objective optical system.

15. The fundus imaging device according to claim 1,
wherein the first mirror corrects asymmetric distortion of an image plane which occurs due to the second mirror.

16. The fundus imaging device according to claim 1,
wherein the first mirror has the strongest power in the objective optical system.

17. The fundus imaging device according to claim 1,
wherein the scanning optical system includes:
- an SLO optical system that includes a first optical scanner configured to scan light from a first light source, and obtains a front image of the fundus using light from the first light source;
- an OCT optical system that includes a second optical scanner configured to scan measurement light from a second light source, and obtains a tomographic image of the examinee's eye using optical interferometry; and
- an optical path coupling member configured to couple an optical path of the SLO optical system and an optical path of the OCT optical system between the first optical scanner and the first mirror and between the second optical scanner and the first mirror.

18. The fundus imaging device according to claim 17,
wherein the SLO optical system and the OCT optical system are telecentric on an object side.

* * * * *